(12) United States Patent
Tuschl et al.

(10) Patent No.: US 9,005,893 B2
(45) Date of Patent: *Apr. 14, 2015

(54) METHODS TO FIX AND DETECT NUCLEIC ACIDS

(71) Applicant: The Rockefeller University, New York, NY (US)

(72) Inventors: Thomas Tuschl, Brooklyn, NY (US); John Pena, New York, NY (US); Pavol Cekan, New York, NY (US); Cherin Sohn, Rego Park, NY (US); Sara H. Rouhanifard, New York, NY (US); Janos Ludwig, Bonn-Venusberg (DE)

(73) Assignee: The Rockefeller University, New York, NY (US)

( * ) Notice: Subject to any disclaimer, the term of this patent is extended or adjusted under 35 U.S.C. 154(b) by 159 days.

This patent is subject to a terminal disclaimer.

(21) Appl. No.: 13/759,363

(22) Filed: Feb. 5, 2013

(65) Prior Publication Data

US 2013/0130260 A1 May 23, 2013

Related U.S. Application Data

(63) Continuation of application No. 12/721,550, filed on Mar. 10, 2010, now Pat. No. 8,394,588.

(60) Provisional application No. 61/159,288, filed on Mar. 11, 2009.

(51) Int. Cl.
*C12Q 1/68* (2006.01)
*G01N 3/48* (2006.01)
*G01N 1/30* (2006.01)

(52) U.S. Cl.
CPC .............. *G01N 1/30* (2013.01); *C12Q 1/6806* (2013.01); *C12Q 1/6841* (2013.01)

(58) Field of Classification Search
CPC ....... G01N 1/30; C12Q 1/6806; C12Q 1/6841
See application file for complete search history.

(56) References Cited

U.S. PATENT DOCUMENTS

| 4,888,278 A | 12/1989 | Singer et al. |
| 8,394,588 B2 * | 3/2013 | Tuschl et al. ................. 435/6.11 |
| 2004/0180368 A1 | 9/2004 | McGall |
| 2007/0269799 A9 | 11/2007 | Zhang |

OTHER PUBLICATIONS

Farazi et al., "The Growing Catalog of Small RNAs and Their Association with Distinct Argonaute/Piwi Family Members", Development 135 (7), 1201 (2008).
K.S. Kosik, "The Neuronal MicroRNA System", Nat. Rev. Neurosci, 7 (12), 911 (2006).
Landgraf et al., "A Mammalian MicroRNA Expression Atlas based on Small RNA Library Sequencing", Cell, 129 (7), 1401 (2007).
Kloosterman et al., "In Situ Detection of MiRNAs in Animal Embryos Using LNA-Modified Oligonucleotide Probes", Nat. Methods, 3 (1), 27 (2006).
Sokol et al., "Mesodermally Expressed Drosophila MicroNRA-1 is regulated by Twist and is Required in Muscles During Larval Growth", Genes Dev 19 (19) 2343 (2005).
Nelson et al., "RAKE and LNA-ISH Reveal MicroRNA Expression and Localization in Archival Human Brain", RNA, 12 (2), 187 (2006).
Silahtaroglu et al., "Detection of MicroRNAs in Frozen Tissue Sections by Fluorescence in Situ Hybridization Using Locked Nucleic Acid Probes and Tyramide Signal Amplification", Nat. Protoc, 2 (10), 2520 (2007).
Thompson et al., "Analysis of MicroRNA Expression by in Situ Hybridization with RNA Oligonucleotides Probes", Methods, 43 (2), 153 (2007).
G.J. Nuovo, "In Situ Detection of Precursor and Mature MicroRNAs in Paraffin Embedded, Formalin Fixed Tissues and Cell Preparations", Methods 44 (1), 39 (2008).
Bak et al., "MicroRNA Expression in the Adult Mouse Central NervSous System", RNA 14 (3), 432 (2008).
Sempere et al., "Altered MicroRNA Expression Confined to Specific Epithelial Cell Subpopulations in Breast Cancer", Cancer Res., 67 (24) 11612 (2007).
Wang, et al., "The Expression of MicroRNA miR-107 Decreases Early in Alzheimer's Disease and May Accelerate Disease Progression Through Regulation of Beta-Site Amyloid Precursor Protein-Cleaving Enzyme 1", J. Neurosci., 28 (5), 1213 (2008).
Schaefer et al., "Cerebellar Neurodegenertion in the Absence of MicroRNAs", J. Exp. Med, 204 (7), 1553 (2007).
Ryan et al., "MicroRNAs of the Mammalian Eye Display Distinct and Overlapping Tissue Specificity", Mol. Vis, 12, 1175 (2006).
Mansfield, et al., "MicroRNA-Responsive 'Sensor' Transgenes Uncover Hox-Like and other Developmentally regulated Patterns of Vertebrate MicroRNA Expression", Nat. Genet. 36 (10), 1079 (2004).
M.Y. Feldman, "Reactions of Nucleic Acids and Nucleoproteins with Formaldehyde", Prog. Nuclei Acid Res. Mol. Biol., 13, 1 (1973).
Masuda et al., "Analysis of Chemical Modification of RNA from Formalin-Fixed Samples and Optimization of Molecular Biology Applications for Such Samples", Nucleic Acids, Res., 27 (22) 4436, (1999).
Tymianski et al., "A Novel Use for a Carbodiimide Compound for the Fixation of Fluorescent and Non-Fluorescent Calcium Indicators in Situ Following Physiological Experiments", Cell Calcium, 21 (3), 175 (1997).

(Continued)

*Primary Examiner* — James Martinell
(74) *Attorney, Agent, or Firm* — Hoffmann & Baron, LLP

(57) ABSTRACT

In one aspect, the invention relates to a method for fixing a short nucleic acid in a biological sample. In another aspect, the invention relates to a method for detecting a target short nucleic acid in a biological sample. The method includes contacting the biological sample with an aldehyde-containing fixative, and subsequently contacting the sample with a water-soluble carbodiimide. In a further aspect, the invention relates to a kit for fixing a short nucleic acid in a biological sample. The kit includes a support substrate for holding the sample; an aldehyde-containing fixative; and a water-soluble carbodiimide.

15 Claims, 18 Drawing Sheets

(56) References Cited

OTHER PUBLICATIONS

Pall et al., "Carbodiimide-Mediated Cross-Linking of RNA to Nylon Membranes Improves the Detection of siRNA, miRNA and piRNA by Northern Blot", Nucleic Acids Res., 35 (8), e60 (2007).
Kaur et al., "Thermodynamics of DNA-RNA Heteroduplex Formation: Effects of Locked Nucleic Acid Nucleotides Incorporated into the DNA Strand", Nucleic Acids Symp. Ser., 52, 425 (2008).
Kye et al., "Somatodendritic MicroRNAs Identified by Laser Capture and Multiplex RT-PCR", RNA 13 (8), 1224 (2007).
M. Zuker, "Mfold Web Server for Nucleic Acid Folding and Hybridization Prediction", Nucleic Acids Res., 31 (13), 3406 (2003).
Danziger et al., "Tables of Distribution-Free Tolerance Limits", Annals of Mathematical Statistics, 35 (3), 1361 (1964).
Lein et al., "Genome-Wide Atlas of Gene Expression in the Adult Mouse Brain", Nature, 445 (7124) 168 (2007).
Abramoff et al., "Image Processing with ImageJ", Biophotonics International, 11 (7), 36 (2004).
Hafner et al., "Identification of MicroRNAs and other Small Regulatory RNAs Using cDNA Library Sequencing", Methods, 44 (1) 3, (2008).
Chu, et al., "Derivatization of Unprotected Polynucleotides", Nucleic Acids Research, 11 (6), 6513 (1983).
Tech Tip #30, "Modify and Label Oligonucleotide 5' Phosphate Groups", Pierce Biotechnology, Inc. pp. 1-2 (2006).
Tuschl et al., "Keystone Seminar" pp. 1-35, Mar. 28, 2008.
Pena et al., Nature Methods 6 (2), 139 (2009).
Ahern, The Scientist 9 (15), 20, (1995).

* cited by examiner

Figure 18

Ethyl-3-(3-Dimethylaminopropyl)carbodiimide

N,N'-Diisopropylcarbodiimide

1,3-Bis(2,2-dimethyl-1,3-dioxolan-4-ylmethyl) carbodiimide

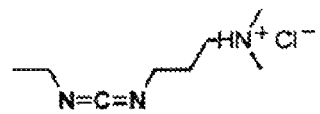

EDC-HCl
Ethyl-3-(3-Dimethylaminopropyl) carbodiimide hydrochloride

1,3-Bis(trimethylsilyl)carbodiimide

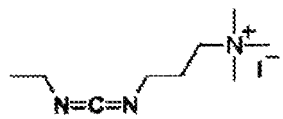

Ethyl-3-(3-Dimethylaminopropyl) carbodiimide methiodide

1,3-Di-p-tolylcarbodiimide

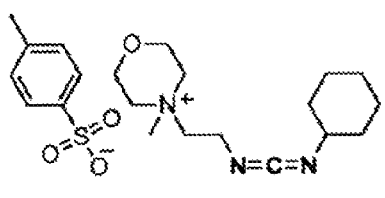

CMC
N-Cyclohexyl-N'-(2-morpholinoethyl) carbodiimide metho-p-toluenesulfonate

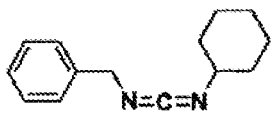

N-Benzyl-N'-cyclohexylcarbodiimide

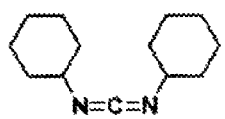

DCC
N-N'-Dicyclohexylcarbodiimide

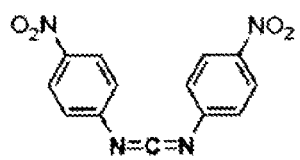

N-N'-Bis(4-nitrophenyl)carbodiimide

METHODS TO FIX AND DETECT NUCLEIC ACIDS

CROSS-REFERENCE TO RELATED APPLICATIONS

This application is a continuation of U.S. application Ser. No. 12/721,550, filed on Mar. 10, 2010, issued as U.S. Pat. No. 8,394,588 on Mar. 12, 2013, which claims priority from U.S. Provisional Application Ser. No. 61/159,288 filed on Mar. 11, 2009, all of which are incorporated herein by reference.

The invention was made with U.S. Government support under contract number GM073047, EY18082-01A2 and MH080442. Accordingly, the U.S. Government has certain rights in the invention.

BACKGROUND OF THE INVENTION

Association studies are rapidly linking miRNAs with cancer and neurological disorders. miRNAs have specific expression and function in specialized cell types, emphasizing the need to define cell-type-specific miRNA expression patterns. The most common method for visualizing gene expression in specific cell types is in situ hybridization (ISH).

However, conventional ISH methods permit the release and diffusion of small nucleic acids, such as miRNA, from tissue. Therefore, there remains a need for an improved method to fix and detect small nucleic acids in a tissue sample.

SUMMARY OF THE INVENTION

In one aspect, the invention relates to a method for fixing a short nucleic acid in a biological sample. The method includes contacting the biological sample with an aldehyde-containing fixative, and subsequently contacting the sample with a water-soluble carbodiimide.

In another aspect, the invention relates to a method for detecting a target short nucleic acid in a biological sample. The method includes contacting the biological sample with an aldehyde-containing fixative; subsequently contacting the sample with a water-soluble carbodiimide to produce a crosslinked short nucleic acid; contacting the cross-linked miRNA with a probe, said probe being complementary to all or a part of a region of interest of the short nucleic acid, thereby producing a hybridized short nucleic acid; and detecting the hybridized short nucleic acid as the target short nucleic acid.

In a further aspect, the invention relates to a kit for fixing a short nucleic acid in a biological sample. The kit includes a support substrate for holding the sample; an aldehyde-containing fixative; and a water-soluble carbodiimide.

BRIEF DESCRIPTION OF THE DRAWINGS

FIG. 18: EDC derivatives. The water-soluble core of carbodiimides, which is responsible for the crosslinking is shown bold.

DETAILED DESCRIPTION OF THE INVENTION

Method for Fixing

Figure 1:
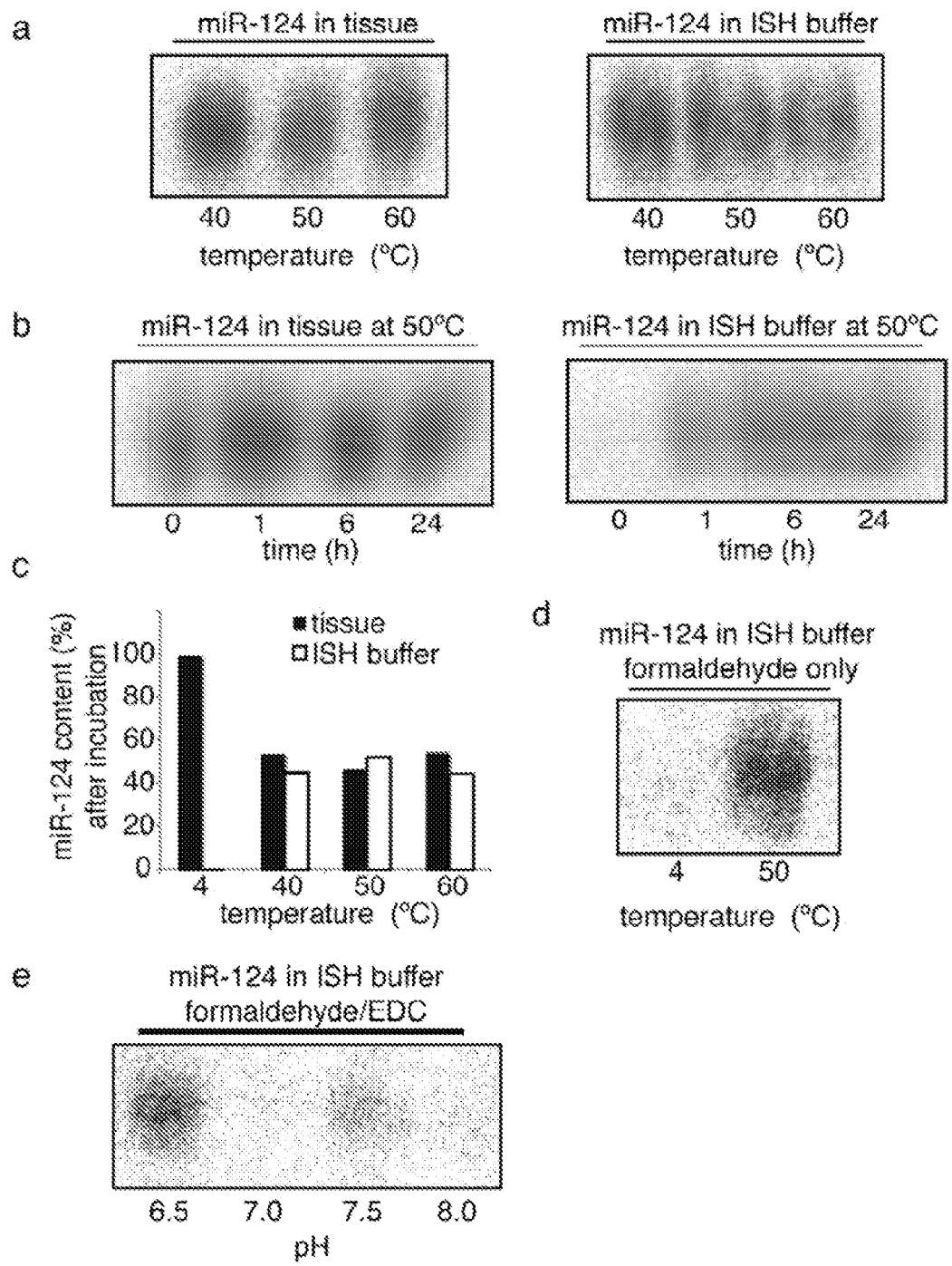
FIG. 1: miRNAs retained in formaldehyde+EDC-fixed tissues. (a) Northern blotting analysis shows escape of miR-124 from formaldehyde-fixed tissues into ISH buffer after 24 h incubation at temperatures of 40° C. and higher. (b) Time course of hybridization at 50° C. shows miR-124 accumulates in ISH buffer after 1 h. (c) Quantification of Northern blots show approx. 50% of miR-124 were present in the hybridization buffer after overnight incubation, P<0.05, n=3. (d) At 4° C., miR-124 was not detectable in the hybridization buffer, which would suggest that RNA-protein crosslinks were intact at lower temperatures. (e) Samples fixed with formaldehyde+ EDC show negligible amounts of miR-124 in ISH buffer at pH 7.0 and 8.0.

In one aspect, the invention relates to a method for fixing a short nucleic acid in a biological sample. The method includes contacting the biological sample with an aldehyde-containing fixative, and subsequently contacting the sample with at least one of the following agents: a water-soluble carbodiimide or cyanogen bromide.

"Fixing" as used herein refers to immobilizing a short nucleic acid within the biological sample "Immobilizing" as used herein refers to binding the short nucleic acid to the biological sample such that the binding is sufficient to be stable under conditions of washing, probing, labeling, and/or analysis.

A "nucleic acid" or "oligonucleotide" or "polynucleotide" refers to at least two nucleotides covalently linked together. The nucleic acid may be any type of nucleic acid, such as DNA or RNA. Exemplary nucleic acids include mRNA, tRNA, rRNA, shRNA, siRNA or Piwi-interacting RNA, or a pri-miRNA, pre-miRNA, miRNA, snoRNA, long ncRNAs, anti-miRNA, and any variants thereof. Additional nucleic acids include genomic DNA, cDNA, or a hybrid wherein the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Further examples of nucleic acids include DNA or RNA of a virus, or nucleic sequences derived from a virus genome. In one embodiment, the nucleic acid is a short DNA or RNA molecule derived from a degraded source, such as, for example, degraded mRNA.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides and nucleic acids may also include locked nucleic acids (LNA), as described in U.S. Patent Application No. 20020115080, which is incorporated herein by reference.

Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs, and mixtures of naturally occurring nucleic acids and analogs may be made.

A nucleic acid may include variants thereof. A "variant" as used herein refers to (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

Nucleic acids may be single stranded or double stranded, or may contain portions of both double stranded and single stranded sequence. Nucleic acids may be synthesized as a single stranded molecule or expressed in a cell (in vitro or in vivo) using a synthetic gene. Nucleic acids may be obtained by chemical synthesis methods or by recombinant methods.

A nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

A "short" nucleic acid refers to a nucleic acid that has a maximum number of base pairs in length of about 100, 90, 80, 70, 60, 50, 40, 35, 34, 33, 32, 31, 30, 29, 28, 27, 26, 25, 24, 23, 22, or 21 bp. The short nucleic acid has a minimum number of base pairs in length of about 5, 6, 7, 8, 9, 10, 11, 12, 13, 14, 15, 16, 17, 18, 19, or 20 bp. Any minimum amount can be combined with any maximum amount to define a range for a short nucleic acid.

Exemplary short nucleic acids include mRNA, tRNA, shRNA, siRNA or Piwi-interacting RNA, or a pri-miRNA, pre-miRNA, miRNA, and anti-miRNA, or any variants thereof. In one embodiment, the target polynucleotide is a short DNA or RNA molecule derived from a degraded source, such as, for example, degraded mRNA.

In a preferred embodiment, the short nucleic acid is microRNA (miRNA). MicroRNA molecules are known in the art (see, for example, Bartel, *Cell,* 2004, 116, 281-297 for a review on microRNA molecules). The definitions and characterizations of microRNA molecules in the article by Bartel are hereby incorporated by reference. Such molecules are derived from genomic loci and are produced from specific microRNA genes.

miRNAs are typically small RNA molecules of generally about 13-33, 18-24, or 21-23 nucleotides in length. The miRNA may also have a total of at about 5-40 nucleotides in length. These microRNAs are non-coding RNAs which are cleaved from hairpin precursors. miRNAs are naturally 5' phosphorylated and carry 2', 3' dihydroxyl termini. The sequence of the miRNA may comprise the sequence of a miRNA disclosed in U.S. patent application Ser. No. 11/384, 049, 11/418,870 or 11/429,720, the contents of which are incorporated herein, or variants thereof.

A source of the short target nucleic acid is a biological sample. A "biological sample" as used herein refers to a sample of biological tissue or fluid that includes biomolecules. Such samples include, but are not limited to, tissue or fluid isolated from animals or plants. Biological samples also include viruses or unicellular organisms. Biological samples may also include sections of tissues such as biopsy and autopsy samples, frozen sections taken for histologic purposes, hair, and skin. Biological samples also include explants and primary and/or transformed cell cultures derived from animal or patient tissues. Biological samples may also be blood, a blood fraction, plasma, serum, urine, pleural effusion, mucus, ascitic fluid, amniotic fluid, stool, tears, saliva, cerebrospinal fluid, cervical secretions, vaginal secretions, endometrial secretions, gastrointestinal secretions, bronchial secretions, sputum, secretions from ovarian cyst, sperm, secretions from the breast, cell line, or tissue sample.

A biological sample may be provided by removing a sample of cells from an animal, or plant, but can also be accomplished by using previously isolated cells (e.g., isolated by another person, at another time, and/or for another purpose), or by performing the methods described herein in vivo. "Animal" as used herein refers to any animal, including fish, amphibians, reptiles, birds, and mammals, such as mice, rats, rabbits, goats, cats, dogs, cows, apes and humans.

As used herein, the term "biomolecule" in the context of a molecule that binds to a short nucleic acid refers to an entity that can or does bind to a short nucleic acid. Biomolecules include biological molecules, such as a protein, nucleic acid, carbohydrate, fat, and lipid. Exemplary short nucleic acid-binding biomolecules include polypeptides, nucleic acids, small molecules such as hormones, cytokines, and drugs. In one preferred embodiment, the biomolecule is a nucleic acid.

Contacting the Biological Sample with a Fixative

The method includes contacting the biological sample with an aldehyde-containing fixative under conditions in which a biomolecule covalently bonds to a nucleic acid, as is known in the art. Such methods are known in the art. See, e.g., Feldman, "Reactions of nucleic acids and nucleoproteins with formaldehyde," *Prog. Nucleic Acid Res Mol Biol.* 1973, 13:1-49, which is incorporated by reference.

The aldehyde-containing fixative can include an aldehyde-based fixative alone, or in combination with other fixative agents. Exemplary fixative agents include osmium tetroxide, picric acid, dialdehyde starch, AEDP (3-[(2-Aminoethyl) dithio]propionic acid.HCl) ethanol, Ketones, Isocyanate-containing compounds to label hydroxyl-containing molecules, Woodward's reagent K (WRK) (N-ethyl-5-phenylisoxazolium-3'-sulphonate), 1,1'-Carbonyldiimidazole (CDI), Bis[2-(N-succinimidyl-oxycarbonyloxy)ethyl]sulfone (BSOCOES) and sulfo-BSOCOES, Ethylene glycol-bis(succinic acid N-hydroxysuccinimide ester) EGS, Sulfo-EGS, N,N'-Disuccinimido Carbonate (DSC), Imidoester. Modification of the 5' phosphate using EDC and other coupling reagents, Cystamine followed by DTT and a sulfhydryl crosslinker. (N-Succinimidyl 3-(2-pyridyldithio)-propionate) and LC-SPDP (Succinimidyl 6-(3-[2-pyridyldithio]-propionamido)hexanoate), SPDP modification of amines coupled to the 5' phosphate of nucleotides followed by a reducing agent, DTT, creating a sulfhydryl group attachment, and a sulfhydryl crosslinker. SATA to modify a 5'-amine derivative of oligonucleotides, forming a protected sulfhydryl for crosslinking.

Examples of an aldehyde-based fixative agent includes, for example, formaldehyde, a derivative of formaldehyde, paraformaldehyde, glyoxal, and glutaraldehyde.

Contacting the Biological Sample with a Water-Soluble Carbodiimide or Cyanogen Bromide Subsequent to the step of contacting a biological sample with an aldehyde-containing fixative, the method includes contacting the sample with at least one of the following agents: a water-soluble carbodiimide or a cyanogen halide. A water-soluble carbodiimide is preferred.

Exemplary water-soluble carbodiimides include 1-Ethyl-3-(3-Dimethylaminopropyl)-Carbodiimide (EDC), 1-Ethyl-3-(3-Dimethylaminopropyl)-Carbodiimide Hydrochloride, 1-Cyclohexyl-3-(2-morpholinyl-(4)-ethyl)carbodiimide metho-p-toluenesulfonate (CMC), N,N'-dicyclohexylcarbodiimide (DCC), and N,N'-diisopropylcarbodiimide (DIC), and derivatives thereof. Examples of derivatives of water-soluble carbodiimides include those illustrated in FIG. 18. In one embodiment, the water-soluble carbodiimide is 1-Ethyl-3-(3-Dimethylaminopropyl)-Carbodiimide (EDC).

Examples of cyanogen halides include cyanogen bromide, cyanogen fluoride, cyanogen chloride, cyanogen iodide. Cyanogen bromide is preferred.

In another embodiment, the method includes contacting the sample with a water-soluble carbodiimide, followed by a cyanogen halide. For example, the method may include contacting the sample with an aldehyde-containing fixative, then subsequently contacting the sample with 1-Ethyl-3-(3-Dimethylaminopropyl)-Carbodiimide or 1-Ethyl-3-(3-Dimethylaminopropyl)-Carbodiimide Hydrochloride, then with cyanogen bromide.

In a further embodiment, the water-soluble carbodiimide and/or cyanogen halide are in solution with a buffer. An exemplary buffer for a water-soluble carbodiimide includes 1-methylimidazole buffer, and an exemplary buffer for a cyanogen halide includes N-morpholinoehanesulfonate (MES) buffer.

The water-soluble carbodiimide and/or cyanogen halide solution has a pH greater than 6.0 and less than 9.0. Preferably, the pH of the water-soluble carbodiimide and/or cyanogen halide solution has a pH of about 7.0 to 8.5. In a preferred embodiment, the water-soluble carbodiimide is EDC and the pH of the EDC solution is about 8.0. In another preferred embodiment, the cyanogen halide solution has a pH of about 7.0.

In one embodiment, the water-soluble carbodiimide has a concentration of about 50 mM to about 250 mM. In another embodiment, the water-soluble carbodiimide contacts the sample at a temperature of about 20° C. to about 70° C.

In one embodiment, the cyanogen halide has a concentration of about 10 mM to about 500 mM. In another embodiment, the cyanogen halide contacts the sample at a temperature of about 0° C. to about 40° C.

Method for Detecting

In another aspect, the invention relates to a method for detecting a short target nucleic acid in a biological sample. The method includes contacting the biological sample with an aldehyde-containing fixative and subsequently contacting the sample with a water-soluble carbodiimide or cyanogen bromide to produce a cross-linked short nucleic acid. The method further includes contacting the cross-linked short nucleic acid with a probe, said probe being complementary to all or a part of a region of interest of the short nucleic acid, thereby producing a hybridized short nucleic acid. The method also includes detecting the hybridized short nucleic acid as the short target nucleic acid.

"Detecting" refers to determining the presence of a component in a sample. Detection may also mean determining the absence of a component. Detection may also mean measuring the level of a component, either quantitatively or qualitatively.

A "target nucleic acid" as used herein refers to any nucleic acid that is to be identified, fixed, or otherwise analyzed. The target nucleic acid may be any type of nucleic acid, such as DNA or RNA. Exemplary target nucleic acids include DNA or RNA of a virus, or nucleic sequences derived from a virus genome. Exemplary target nucleic acids include mRNA, tRNA, shRNA, siRNA or Piwi-interacting RNA, or a pri-miRNA, pre-miRNA, miRNA, and anti-miRNA, or any variants thereof. In one embodiment, the target polynucleotide is a short DNA or RNA molecule derived from a degraded source, such as, for example, degraded mRNA.

As stated above, subsequent to fixing or cross-linking, the method includes contacting the cross-linked short nucleic acid with a probe. In one embodiment, one or more than one probe may be used to bind to the target nucleic acid.

In a preferred embodiment, the probe is a polynucleotide of single- or double-stranded DNA or RNA. For example, a probe may be single stranded or partially single and partially double stranded. The strandedness of the probe is dictated by the structure, composition, and properties of the target sequence.

The probe is capable of binding to a target nucleic acid of complementary sequence or a substantially complementary sequence through one or more types of chemical bonds, usually through complementary base pairing, usually through hydrogen bond formation. Probes may bind to target nucleic acid without complete complementarity to the probe sequence, depending upon the stringency of the hybridization conditions.

In a preferred embodiment, the probe has 100% complementarity to all or a portion of a region of interest of the target nucleic acid. "Complement" or "complementary" as used herein refers to Watson-Crick (e.g., A-T/U and C-G) or Hoogsteen base pairing between nucleotides or nucleotide analogs of nucleic acid molecules.

"Substantially complementary" used herein may mean that a first sequence is at least 50%, 55%, 60%, 65%, 70%, 75%, 80%, 85%, 90%, 95%, 97%, 98% or 99% identical to the complement of a second sequence over a region of 2, 3, 4, 5, 6, 7, 8, 9, 10, 11, 12, 13, 14, 15, 16, 17, 18, 19, 20-40, 40-60, 60-100, or more nucleotides, or that the two sequences hybridize under stringent hybridization conditions.

The site on the target nucleic acid on which the probe binds is the "target binding site." The target binding site may be 5-100 or 10-60 nucleotides in length. The target binding site may include a total of 5, 6, 7, 8, 9, 10, 11, 12, 13, 14, 15, 16, 17, 18, 19, 20, 21, 22, 23, 24, 25, 26, 27, 28, 29, 30-40, 40-50, 50-60, 61, 62 or 63 nucleotides. Any minimum amount can be combined with any maximum amount to define a range for a target binding site.

The probe is preferably contacted to the biological sample under stringent hybridization conditions. "Stringent hybridization conditions" used herein may mean conditions under which a first nucleic acid sequence (e.g., probe) will hybridize to a second nucleic acid sequence (e.g., target nucleic acid), such as in a complex mixture of nucleic acids. Stringent conditions are sequence-dependent and will be different in different circumstances. Stringent conditions may be selected to be about 5-10° C. lower than the thermal melting point ($T_M$) for the specific sequence at a defined ionic strength pH. The $T_M$ may be the temperature (under defined ionic strength, pH, and nucleic concentration) at which 50% of the probes complementary to the target hybridize to the target sequence at equilibrium (as the target sequences are present in excess, at $T_M$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.5 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

The DNA or RNA probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe is preferably about 10 to 30 nucleotides in length, more preferably 18-25 nucleotides in length. Any minimum amount can be combined with any maximum amount to define a range for a probe.

The probe may be directly labeled or indirectly labeled. A "label" as used herein refers to a composition that is detectable by spectroscopic, photochemical, biochemical, immunochemical, chemical, and/or physical means. For example, suitable labels include $^{32}P$, fluorescent dyes, electron-dense reagents, enzymes (e.g., as commonly used in an ELISA), biotin, digoxigenin, or haptens and other molecules that can be made detectable.

The label may be a fluorophore, such as described in U.S. Pat. No. 6,541,618. The label may also be a quencher molecule, which when in proximity to another label, may decrease the amount of detectable signal of the other label, such as described in U.S. Pat. No. 6,541,618. The label may be incorporated into nucleic acids and proteins at any position of the nucleic acids or proteins.

Examples of direct labeling, such as Chemical labeling, include Kreatech ULS chemical labeling technology, which labels miRNA or probes or target nucleic acids with biotin. Another example of direct labeling is part of a PerkinElmer Micromax™ Direct Labeling Kit, which labels miRNAs with biotins along the length of the miRNA. An example of enzymatic End labeling includes ligation of dinucleotides with a biotin entity (pCU-bio). Signal amplification, such as Tyramide signal amplification (TSA) amplifies the number of biotins in site, starting from one biotin to which a Streptavidin-horse radish peroxidase (HRP) conjugate is bound. The Tyramide biotin substrate is processed by the HRP to produce a non soluble biotin that is precipitated in site, creating a cluster of biotins on the appropriate microsphere.

In one embodiment, the probe includes a locked nucleic acid (LNA), as described in U.S. Patent Application No. 20020115080, which is incorporated herein by reference. Exemplary probes include about 5 to 8 LNAs.

The probe may further include a linker. The linker may be 10-60 nucleotides in length. The linker may be 20-27 nucleotides in length. The linker may be of sufficient length to allow the probe to be a total length of 45-60 nucleotides. The linker may not be capable of forming a stable secondary structure, may not be capable of folding on itself, or may not be capable of folding on a non-linker portion of a nucleic acid contained in the probe. The sequence of the linker may not appear in the genome of the animal from which the probe non-linker nucleic acid is derived.

In addition to contacting the cross-linked short nucleic acid with a probe, the method may further include contacting the biological sample with a probe complementary to all or a part of a region of interest of another target nucleic acid in the biological sample, thereby producing a hybridized target nucleic acid. Accordingly, in one embodiment, more than one target nucleic acid may be hybridized with a probe and identified. In a further embodiment, multiple probes with different labels can be hybridized to different target nucleic acids. For example, a probe can be used that hybridizes to a miRNA of interest, concurrently with another probe that hybridizes to a short nucleic acid that is degraded mRNA and/or an mRNA variant. The identification of a specific probe or a combination of different probes can be used to identify the phenotype of the cell, for example whether the biological sample is a type of cancer.

Kit

In another aspect, the invention relates to a kit for fixing a short nucleic acid in a biological sample. The kit includes a support substrate for holding the sample, an aldehyde-containing fixative, and at least one the following agents: a water-soluble carbodiimide or cyanogen bromide.

A "support substrate" refers to a composition that is amenable to at least one detection method and contains individual sites that are appropriate for attachment or association of the biological sample, probe, and nucleic acid. Exemplary support substrates include glass, modified or functionalized glass, plastics (including acrylics, polystyrene and copolymers of styrene and other materials, polypropylene, polyethylene, polybutylene, polyurethanes, Teflon J, etc.), polysaccharides, nylon or nitrocellulose, resins, silica or silica-based materials including silicon and modified silicon, carbon, metals, inorganic glasses and plastics. The substrates may allow optical detection without appreciably fluorescing.

Preferably, the support substrate is one to which the biological sample may be bound. The binding of the biological sample to the support substrate may be covalent or non-covalent. Covalent bonds may be formed directly between the probe or biological sample and the solid support or may be formed by a cross-linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

The kit may also include any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein. For example, the kit may be a kit for the fixation, amplification, detection, identification or quantification of a target nucleic acid sequence.

Other aspects of the invention will become apparent to the skilled artisan by the following description of the invention.

EXAMPLES

The following examples are set forth to illustrate the present invention, and are not to be construed as limiting thereof.

General Methods

Microscopy and Image Processing

Images were captured on an Olympus BX50 microscope equipped with a DP70 camera and Olympus DP controller software. For florescent imaging we used the following filter sets; U-MWU2 (Olympus) for DAPI, 41001 HQ (Chroma) for Fluoro488, 49004 ET (Chroma) for Cy3. The images from both the immunohistochemistry and the ISH were captured using DP70 camera and processed using Olympus Microsuite Five software (Olympus).

Northern Blotting

Northern blotting was performed as described1 using Hybond-N+ membrane (Amersham GE healthcare), and the hybridization and wash steps were performed at 50° C. The oligodeoxynucleotide probes were 5'-labelled with [γ-32P] ATP. The probe for miR-124 was 5' TTGGCATTCAC-CGCGTGCCTTA. To control for loading of the gel, 5S rRNA was detected by ethidium bromide staining of the polyacrylamide gel prior to transfer. Probed samples were recorded by phosphoimaging and quantified. Northern blotting images were quantified using ImageJ software5.

miRNA Cloning and Sequencing

RNA was extracted from dissected mouse brain regions and size-fractionated by a denaturing PAGE. miRNA cloning was performed as described previously6. The cDNA library was sequenced by 454 sequencing. miRNA sequences were annotated as described1 and obtained about 90,000 sequence clones.

Supplemental Methods

Design and Synthesis of LNA-Modified Oligodeoxynucleotide Probes

LNA-spiked oligodeoxynucleotide probes (LNAs) were identical in length and fully complementary to the predominantly cloned mature miRNA or miRNA* sequence1. On average, we placed 5 to 8 LNA residues in a 22-nt oligodeoxynucleotide probe. To optimize probe hybridization, we avoided inserting LNA bases in positions that may stabilize internal secondary structures, so LNA residues were placed outside of predicted secondary self-structures. The LNA probe sequences are listed in Supplementary Table 1. Probes were synthesized at 0.2 or 0.4 mmol scale on an ABI 3400 DNA synthesizer using 3'-amino-modifier C7 CPG (500 Å) solid glass support (Glen Research) and LNA and DNA phosphoramidites (Sigma-Proligo and Glen Research). The aminolinker Fmoc and phosphate cyanoethyl protecting groups were removed by gently passing back and forth 3 ml of freshly prepared 20% piperidine (Sigma) in N,N-dimethylformamide (DMF, Sigma) for 5 min over each column Columns were washed three times with 3 ml of acetonitrile and dried with pressurized air. For further deprotection, the CPG was transferred to a 1.5 ml screw cap tube and incubated with 1.2 ml of 28% aqueous ammonium hydroxide solution for 16 h at 55° C. The tube was placed on ice for 5 min, and the supernatant transferred to a 13 ml centrifugation tube. 10 ml of 1-butanol was added, vigorously mixed and the LNA pellet was collected by centrifugation at 13,000 rpm in an SS-34 rotor at 4° C. for 20 min in Sorvall RC5C Plus centrifuge. The supernatant was removed completely, the pellet dried in an Eppendorf Vacufuge concentrator and redissolved in 282 μl water. In order to exchange ammonium ions with sodium, the LNA solution was adjusted to 0.3 M NaCl by addition of 18 μl of 5 M NaCl and precipitated by addition of 900 μl of 100% ethanol. The pellet was collected by centrifugation and redissolved in 300 μl water. The LNA concentration was determined by measuring its UV absorbance at 260 nm using an average absorbance coefficient of 11,000 M-1cm-1 per nucleotide.

To 3'-digoxigenin-label the LNA probe, an aliquot corresponding to 30 nmol of the LNA was dried in an Eppendorf concentrator and redissolved in 50 μl of 100 mM sodium carbonate buffer at pH 8.5. 240 nmol of digoxigenin-3-O-methylcarbonyl-ε-aminocaproic acid-N-hydroxysuccinimide ester (Roche) freshly dissolved in 50 μl anhydrous DMF was added, mixed and incubated for 16 h at 25° C. The yield of a typical labeling reaction was 80%. The DIGlabeled probes, which showed reduced mobility compared to the starting material, were separated on a 43×23×0.2 cm denaturing 18% PAGE gel (200 ml gel volume) for 6 h at 50 W. Product bands were visualized by UV shadowing, excised, and eluted from the gel slice overnight into 3 volumes (w/v) of 0.3 M NaCl, ethanol precipitated and resuspended in 100 μl water.

DIG-labeling was examined by spotting 1 pmol, 100 fmol and 10 fmol on a Nylon membrane (Amersham Hybond-N+) followed by incubation of the membrane with anti-DIG antibody fragment conjugated to peroxidase antibody (Roche) with NBT/BCIP (Roche). Formazan Blue deposition is observed between 10 min to 1 h for all amounts spotted.

UV Melting Profiles of miRNA-LNA-Probe Duplexes

The UV absorbance change associated with melting of the LNA probe and miRNA duplex was recorded at 280 nm on an Uvikon UV/VIS spectrophotometer (LifePower software) equipped with temperature-controlled cuvette holders. The rate of cuvette heating and cooling was 0.3° C./min and the absorbance was recorded every min. The melting temperature (TM) of duplex formation was obtained by curve-fitting the absorbance change as a function of temperature to a two-state model using Meltwin 3.5 software. To prepare samples for $T_M$ analysis, miRNA+probe pairs in a volume of 300 µl of 1.5 µM of unlabeled LNA probe and 1.5 µM of synthetic miRNA in 750 mM NaCl, 75 mM sodium citrate, 50 mM sodium phosphate (pH 7.0) and 50% formamide were incubated for 5 min at 95° C., for 5 min at 80° C., gradually cooled for 3 h to 50° C., and then held at room temperature for 1 h or longer. The solution was then transferred to a quartz cuvette, overlayed with 500 µl mineral oil (Sigma) and degassed for 10 min by applying a vacuum to a small dessicator holding the cuvettes. Adjusted Parameters for Prediction Programs to Estimate $T_M$ for miRNA-LNA Probe Duplex in Formamide Containing ISH Buffer.

To best emulate our experimental $T_M$ analysis and introduce a correction factor, we tested several salt concentrations in the prediction program (lna-tm.com) and determined that 50 mM salt, instead of the actual 750 mM present in ISH buffer, yielded very similar values with an average predicted $T_M$ of 0.26° C. higher than the average of our experimental values with a standard deviation of 4.4° C., based on a sample of 127 miRNA-LNA probe duplex melting profiles. To derive estimates for the likelihood that the predicted $T_M$ error will fall within a specified range, we constructed nonparametric prediction intervals. We found that with 95.3% probability, the error in the predicted $T_M$ for any miRNA-LNA probe pair will fall between −9.2° C. and 8.6° C. With 68.8% probability, the predicted $T_M$ error will fall between −4.1° C. and 4.7° C. Within a broad range of ±2 standard deviations of the mean, the sampled distribution of predicted $T_M$ errors is closely approximated by a normal distribution with µ=0.26° C. and σ=4.4° C. We therefore repeated the same analysis under the assumption of normality and found closely similar results. We found that with a 95.3% probability, the error in the predicted $T_M$ for any miRNA-LNA pair falls within −9.2° C. and 8.6° C. of the experimental $T_M$ in formamide-containing ISH buffer or a 68% probability that the true $T_M$ will fall between −3° C. and 5.1° C.

Tissue Preparation and Processing

Male, 2-month-old C57BL/6J mice (Jackson Labs) were maintained on a 12 h light/dark cycle Animals were sedated in accordance with NIH Animal Welfare guidelines using ketamine and xylazine cocktail before organ perfusion with 50 ml of Tris-HCl buffered Saline (TBS) containing 50 mM Tris-HCl, 150 mM NaCl and the pH adjusted to 7.4. Immediately after TBS, we perfused with 30 ml of 4% paraformaldehyde (PFA) in TBS. Tissues were collected, immersed in 30 ml of 4% PFA in TBS for 24 h at 4° C., then in 30 ml of 0.5 M sucrose diluted in TBS at 4° C. for 48 h. The tissues were mounted in Tissue-Tek OCT Compound, frozen in a dry-ice+ ethanol bath in a Cryomold (Tissue-Tek), immediately serial sectioned from 5 to 40 µm with a cryostat (Leica) and mounted on SuperFrost Plus glass slides (Thermo Fisher Scientific). Unprocessed specimen or mounted slides can also be stored at −80° C.

In Situ Hybridization Procedure

Processing or wash steps were generally carried out by placing up to 20 slides in 75 ml glass Coplin jars (Electron Microcopy Sciences) filled with specified solutions and all wash steps were in 50 ml of the stated solution for 5 min at 25° C., unless otherwise noted. Tissue sections mounted on glass slides were thawed and air-dried for 1 h at 25° C. and then incubated in a 75 ml solution containing 20 µg/ml proteinase K (Roche) in TBS, pH 7.4 for 20 min. Thereafter, the slide was washed two times in 75 ml TBS. Samples were fixed in 75 ml of 4% PFA in TBS for 10 min, washed with 0.2% (w/v) glycine in TBS, and washed two times in 75 ml TBS. To remove residual phosphate from the TBS washes, slides processed with EDC fixation were incubated twice for 10 min in 75 ml of a freshly prepared solution containing 0.13 M 1-methylimidazole, 300 mM NaCl, pH 8.0 adjusted with HCl. To prepare 160 ml of imidazole buffer, add 1.6 ml of 1-methylimidazole to 130 ml water, adjust the pH by adding approximately 450 µl 12 M HCl to pH 8.0, then add 16 ml 3 M NaCl and water to a final volume of 160 ml. In the meantime, prepare a solution of 0.16 M 1-ethyl-3-(3-dimethylaminopropyl) carbodiimide (EDC) (Sigma) by adding 176 µl EDC into 10 ml of 1-methylimidazole+300 mM NaCl (pH 8.0) solution, and then readjust the pH of the EDC solution by further addition of approximately 100 µl 12 M HCl to pH 8.0. It is important for storage of commercial EDC to handle the reagent under anhydrous conditions and protect it with a layer of argon. Aqueous solutions containing EDC and/or 1-methylimidazole cannot be stored. Place slides in a humidified chamber and add 500 µl of EDC solution to each slide and incubated for 1 to 2 h at 25° C. The slides were washed in 0.2% (w/v) glycine/TBS and then washed twice in TBS.

For inactivation of enzymes in tissues, e.g. alkaline phosphates and peroxidases, slides were acetylated by incubating for 30 min in a 75 ml solution of freshly prepared 0.1 M triethanolamine and 0.5% (v/v) acetic anhydride. Slides were then rinsed twice in TBS. For pre-hybridization, the tissue sections on the slides were covered with 500 µl of hybridization buffer containing 50% formamide, 5×SSC, 5×Denhardt's solution (Applichem), 250 µg/ml yeast tRNA (Sigma), 500 µg/ml salmon sperm DNA (Sigma), 2% (w/v) Blocking Reagent (Roche), 0.1% 3-[(3-Cholamidopropyl) dimethylammonio]-1-propanesulfonate (CHAPs) (Sigma), 0.5% Tween at 25° C. for 2 h in a humidified chamber. The hybridization buffer was removed by tilting the slide.

For hybridization, 4 pmol of DIG-labeled LNA probe diluted in 100 µl of hybridization buffer were applied per section, and covered with coverslips (LifterSlips, Fisher). The slides were incubated in a sealed humidified chamber for 16 h at a temperature 20° C. below the $T_M$ of the experimentally determined miRNA-LNA probe duplex. Hybridization conditions were adjusted 20° C. below the LNA probe's experimentally determined $T_M$, taking into account that the probe concentration for an ISH experiment is 40 nM compared to 1.5 µM required for optical $T_M$ Measurements.

The slides were immersed in 20 ml of 5×SSC at 25° C. so the coverslip can be removed and then washed twice in 75 ml of a solution containing 50% formamide, 1×SSC, and 0.1% Tween for 30 min at the same temperature as probe hybridization. Finally slides were washed in 75 ml 0.2×SSC for 15 min and once in 75 ml of 0.1% Tween in TBS. To inactivate endogenous peroxidase activity, slides were incubated in 75 ml of 3% hydrogen peroxide in TBS with 0.1% Tween for 30 min, followed by three 1 min washes of TBS/0.1% Tween. In preparation for probe detection, 500 µl of blocking solution containing 0.5% Blocking Reagent (Roche), 10% heat inactivated goat serum, and 0.1% Tween 20 in TBS was applied to each slide for 1 h at 25° C., then incubated in anti-DIG-FAB peroxidase (POD) (Roche) diluted 1:500 in blocking solution for 1 h at 25° C. Slides were then washed as described below in preparation for the application of the various detection reagents.

Cy3 Fluorescent Detection System

The slides were washed twice in a solution containing 0.1% Tween 20, in TBS and 200 µl of TSA Plus Cy3 System working solution was applied onto to the sections for 10 min at 25° C. in the dark according to the manufacturer's protocol (PerkinElmer Life Sciences). The slides were then washed three times in TBS with a tilting rotator. The slides were mounted using 2 drops of Vectashield mounting medium with DAPI (Vector Laboratories) and samples processed for microscopy.

Alkaline Phosphatase Double Amplification Detection System

This detection method was adapted from studies by Lein et al. The slides were washed three times in 75 ml in TNT buffer, consisting of 0.1M Tris-HCl, pH 7.5, 0.15 M NaCl, and 0.1% Tween 20. Thereafter, 250 µl of biotinylated tyramide solution from the Individual Indirect Tyramide Reagent kit (PerkinElmer Life Sciences) was applied to each slide for 30 min at 25° C., according to the manufacturer's protocol. The slides were washed three times in 75 ml maleate buffer (0.09 M maleic acid, 0.175 M NaOH, 1 M NaCl, 0.5% Tween 20, pH 7.5). A 1:500 solution of 350 µl of NeutrAvidin-conjugated alkaline phosphatase (Thermo Scientific) in maleate buffer supplemented with 10 mg/ml blocking reagent (Roche) was applied to the slide for 40 min at 25° C. Slides were then washed twice in 75 ml maleate buffer, and four times in 75 ml TMN buffer (0.1 M Tris base, pH 9.5, 0.05 M MgCl2, 0.5 M NaCl, 0.5% Tween 20, 2 mM (−)-tetramisole hydrochloride). The formazan deposition was performed by applying 200 µl of a solution containing 0.375 mg/ml Nitro blue tetrazolium chloride (NBT) (Roche) and 0.188 mg/ml of 5-Bromo-4-chloro-3-indolyl phosphate, toluidine salt (BCIP) (Roche) in TMN buffer. Upon deposition of the blue pigment, typically visible after 30 min, the slides were washed twice in 75 ml water, three times in 75 ml of 0.01M Tris-HCl, pH 7.5, 0.5 M NaCl, 5 mM EDTA, 0.05% Tween 20, and incubated for 10 min in 75 ml of 4% aqueous paraformaldehyde solution. Finally, the slides were washed in 75 ml water and mounted using 2 drops of Vectashield mounting medium with DAPI (Vector Laboratories).

Immunohistochemistry and miRNA ISH Co-Staining

To assess whether miR-124 was localized specifically to neurons, brain sections were processed for double immunofluorescence staining to visualize the simultaneous localization of miR-124 (red; Cy3) and a primary antibody for NeuN (green; TRITC), a known neuron-specific nuclear protein. First we performed immunohistochemistry to label neuronal cells. Brain sections mounted on slides were washed three times for 5 min in 50 ml of TBS. Sections were incubated for 1 h in 500 µl of "working solution of M.O.M. Mouse Ig Blocking Reagent" (Vector Laboratories) at 25° C., according to the manufacturer's protocol. Sections were washed twice for 5 min in 50 ml of TBS, followed by incubation in a "working solution of (M.O.M.) diluent" (Vector Laboratories) for 5 min at room temperature, then the "working solution of (M.O.M.) diluent" was removed. To visualize neurons, we incubated the samples with a primary anti-NeuN-clone-A60-AlexaFluor488 conjugated antibody (Chemicon International, Temecula, Calif.) diluted 1:300 in a "working solution of M.O.M. diluent" (Vector Laboratories) for 1 h at 25° C. Slides were then washed 3 times for 5 min in 50 ml of TBS. Slides were mounted using 2 drops of Vectashield mounting medium with DAPI (Vector Laboratories). Please note that the glass coverslips were not sealed, as the samples were later used for ISH to detect miR-124. After image acquisition, coverslips were removed by washes in 50 ml of TBS and the tissue sections were then processed for ISH for miR-124 (Cy3; red) by applying our miRNA ISH protocol described earlier. After miRNA ISH, the sections were mounted using 2 drops of Vectashield mounting medium with DAPI (Vector Laboratories) and samples processed for microscopy.

Photomicrographs of the nuclear staining are required to superimpose images for the immunohistochemistry and the miR-124 ISH. Images were combined to generate an overlay using Olympus Microsuite Five software. Please note that the immunohistochemistry procedure for NeuN protein detection somewhat reduced the efficiency for miRNA detection; performing miRNA ISH before protein staining was not possible as EDC fixation interfered with protein immunohistochemistry.

Small RNA Isolation from Formalin-Fixed Tissue

Formalin-fixed brain tissues used for RNA extraction were cut into 1 mm sections and incubated with a 200 µl solution containing 20 µg/ml proteinase K (Roche) in TBS and incubated at 45° C. for 1 h. The samples were then processed for RNA isolation. Total RNA was isolated from 4% formaldehyde fixed tissue by using the commercial Trizol (Invitrogen) reagent. We added 1 ml of Trizol per 1 mm slice of brain. The mixture was immediately homogenized while kept on ice. Cells were homogenized using a Dounce glass homogenizer (Kimble-Kontes) and then further mechanically homogenized using a Polytron homogenizer (Kinematica AG). Following tissue disruption, 1/10 volume of 3 M sodium acetate (pH 4.2) was added. The mixture was transferred to an Eppendorf tube and centrifuged for 15 min at 12,000 g at 4° C. The aqueous phase was transferred to a new tube without the white interphase. RNA was further extracted with ½ volume of acid-buffered phenol:chloroform:isoamyl alcohol (25:24:1) and centrifuged for 15 min at 4° C. at 12,000 g. Finally, we extracted the aqueous phase with ½ volume chloroform. The upper (aqueous) phase was transferred to a new tube. We added 3 volumes of ethanol to precipitate the RNA and incubated the sample overnight at −20° C. The RNA pellet was collected by centrifugation for 15 min at 4° C. at 12,000 g and the supernatant removed. The pellet was then dissolved in 30 µl water and used for Northern Blotting.

We were unable to isolate miR-124 from the formalin+EDC-treated tissue, presumably because miRNAs remained crosslinked to the protein matrix and the small RNAs were lost to the phenol- or inter-phase during RNA isolation.

Example 1

To better understand the technical challenges associated with miRNA ISH, we investigated the importance of miRNA fixation and probe hybridization. For fixation of proteins and nucleic acids in tissues, a solution containing 3.7% formaldehyde (10% formalin) is commonly used. Formaldehyde crosslinks are reverted by incubation at elevated temperature and this process is facilitated by proteinase K treatment. Reversal of the formaldehyde-based nucleic acid base modifications is also necessary for probe hybridization, but it creates the problem of miRNA release and diffusion out of the tissue sections. Therefore, we examined the extent of miRNA escape from tissue during ISH. We conducted a mock ISH for conventionally fixed brain, isolated RNA from the tissue sections and the ISH buffer, and probed both fractions for the highly expressed neuronal miR-124 by Northern blotting. At hybridization temperatures above 40° C., at least 50% of miR-124 initially present in the tissue section accumulated in the buffer as early as 1 h (FIG. 1a-c). At 4° C., the hybridization buffer showed no signal for miR-124 (FIG. 1d), which would suggest that RNA-protein crosslinks remained intact at lower temperatures.

To prevent the loss of miRNAs, we added an additional miRNA fixation step that uses the miRNA 5' phosphate end, which does not react with formaldehyde. The water-soluble 1-ethyl-3-(3-dimethylaminopropyl) carbodiimide, EDC, reacts with phosphate and condenses it with amino groups in the protein matrix to form stable linkages. When formaldehyde-fixed specimens were additionally treated with EDC, miR-124 no longer escaped from sections, and only trace amounts of miR-124 were detected in the ISH buffer (FIG. 1e). EDC treatment alone, without prior formaldehyde fixation failed to retain miRNAs in tissues (data not shown).

Example 2

Probes that bind to miRNAs with high thermodynamic stability such as DNA probes containing locked nucleic acid (LNA) residues are well suited for miRNA ISH. The melting of LNA-miRNA duplexes can be observed experimentally by UV spectrophotometry. Thermodynamic analysis of LNA-modified deoxynucleotide duplexes led to models that predict their melting temperatures ($T_M$) for any LNA-RNA pair. Unfortunately the $T_M$s cannot be predicted accurately for ISH, as the programs do not consider the presence of formamide denaturant. To derive optimal hybridization conditions, nucleic acid melting studies were conducted and the melting profiles of 130 miRNA-LNA probe pairs were measured. With these data, we provide a correction factor for these programs, by manipulating the salt parameter of LNA-RNA $T_M$ prediction programs, and obtained useful starting points for estimating hybridization temperature in formamide-containing ISH buffer. We generated our LNA probe set based on miRNAs expressed with a clone frequency of at least 0.04% based on small RNA library sequencing from 5 regions of the mouse brain.

Figure 2:
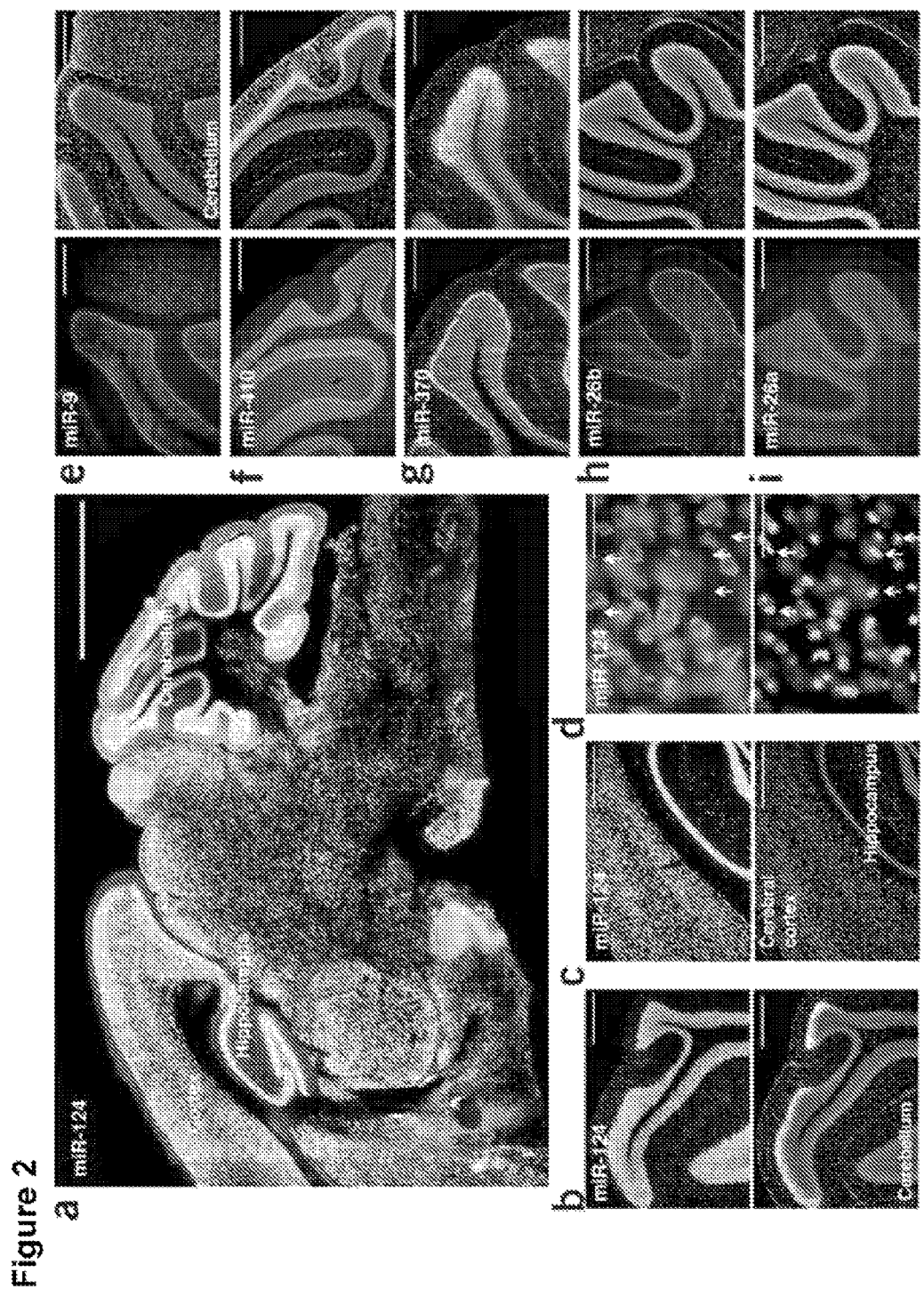
FIG. 2: Visualization of miRNAs expressed at different levels in the mouse brain. (a) Low magnification images of nervous system specific miR-124 shows broad expression in neurons. (b-c) High magnification images of miR-124 demonstrate ubiquitous expression in the neurons of the cerebellum (top, orange), (b) cerebral cortex and hippocampus (c). (d) Higher magnification images show that miR-124 signals are not present in all cells, marked with arrows. (e) Fluorescence images of mouse brain sections probed for highly expressed miR-9 (Cy3, red) localized in Purkinje cells of the cerebellum. (f,g) Image depicting miR-410 (f) and miR-370 (g), which have an intermediate expression. (h,i) Images demonstrate robust signals for miRNAs differing by 3 nucleotides, miR-26b (h) and miR-26a (i) and these miRNAs were differentially expressed. Cell nuclei were counterstained with 4',6-diamino-2-phenylindole dihydrochloride (DAPI, blue; bottom panel of b-d; right panel of e-i). Scale bars, 500 µm (f-i).
Figure 13:
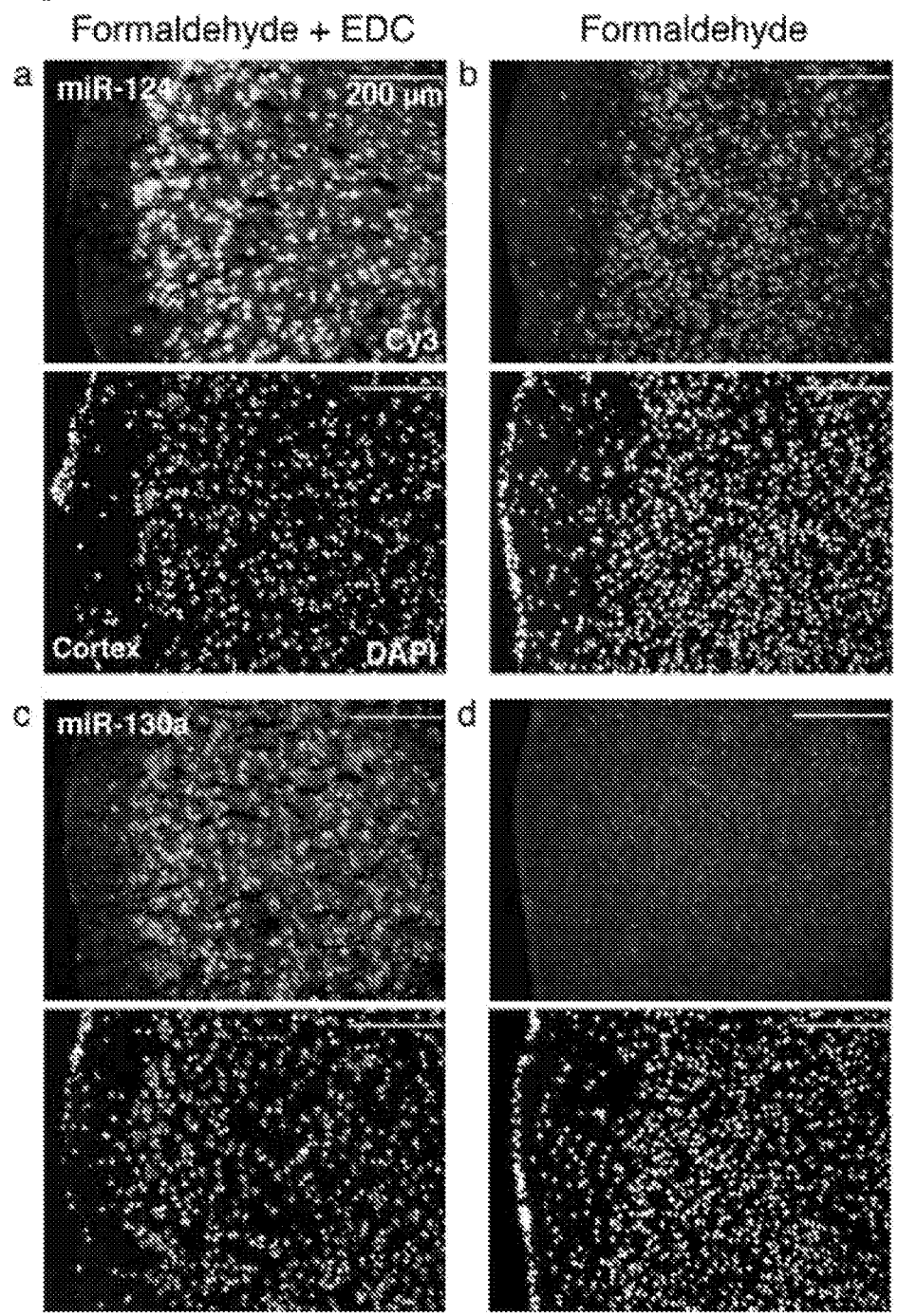
FIG. 13: Comparison of formaldehyde/EDC and conventional formaldehyde fixation for detection of a high and low abundance miRNA in mouse brain by ISH. (a-d) Fluorescence microscopy images of ISH using mouse brain tissue sections fixed with formaldehyde/EDC (left) or conventional formaldehyde alone (right), captured with identical camera settings and exposure times. Highly abundant nervous system specific miR-124 (clone count frequency 8.8%) showed formaldehyde/EDC fixation moderately improved signal intensity (a), compared to formaldehyde fixation alone (b). (c-d) Detection of lower expressed miR-130a (clone count frequency 0.12%) using formaldehyde/EDC (c). Conventional formalin fixed samples showed no signal (d). The digoxigenin-labeled LNA-modified DNA probe was hybridized to a specific miRNA and the signal was amplified using the tyramide-Cy3 detection system. Cell nuclei were counterstained with DAPI (blue; bottom panel). Scale bars were 200 µm.
Figure 14:
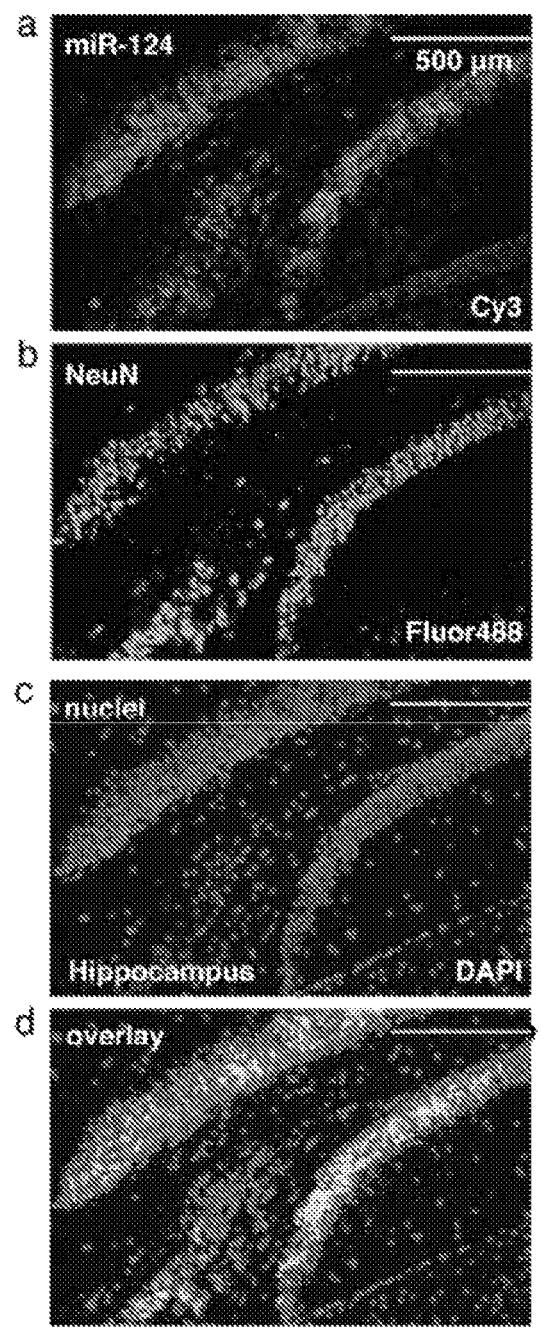
FIG. 14: Images of miR-124 ISH show the majority of staining occurs in neurons. (a) Photomicrograph from ISH of miR-124 (Cy3) in mouse hippocampus (see Supplemental methods for experimental details). (b) Prior to miRNA ISH, samples stained to visualize the localization of neurons with a primary antibody for NeuN (Fluor488), a known neuron-specific nuclear protein. (c) Nuclear staining (DAPI). (d) Overlay of miR-124 (red; Cy3), NeuN (Fluor488), and nuclear staining (DAPI). Scale bars, 200 µm (a-d). Note: double labeling for the miRNA ISH and immunohistochemistry resulted in a weaker signal for both the immunohistochemistry and miRNA ISH.

To determine the range of the ISH sensitivity, we conducted ISH for miRNAs identified at varying frequencies from small RNA cloning libraries in mouse brain; miR-9, 9.3%; miR-124, 8.8%; miR-26a, 3.3%; miR-26b, 0.25%; miR-370, 0.14%; miR-130a, 0.12%; and miR-410, 0.07%. Tissue sections were fixed with formaldehyde+EDC and then ISH performed. We determined the effect of formaldehyde+EDC versus formaldehyde fixation alone by conducting ISH for the most abundant miR-124 and the 73-fold less abundant miR-130a. ISH images show that signal for miR-124 were improved moderately, but miR-130a signals were only detectable in formaldehyde+EDC-fixed samples (FIG. 13). Since the abundant miR-124 presumably retained enough miRNA to nearly saturate the signal, the improvements remained modest, but for lowly expressed miRNAs, loss by diffusion hindered its detection in formaldehyde alone samples. miR-124 is mostly detected in neuronal cells present in different regions of the brain (FIG. 2a-d and FIG. 14) and predominately localized in the cytoplasm, while the cell nuclei were excluded. Another highly expressed miRNA in brain, miR-9, also preferentially localizes in neurons, and is particularly enriched in the Purkinje cell layer (FIG. 2e).

We also observed robust ISH signal for the less abundant miRNAs tested (FIG. 2f-i), with unique miRNA distributions. Interestingly, miR-26a and miR-26b, which differ by 2 nucleotides (C11U, C21U) and originate from different clusters, showed differential expression patterns in the mouse cerebellum (FIG. 2h,i). The absolute signal intensities for the miR-NAs tested were not directly correlated with the abundance of miRNAs and were likely attributed to differences in kinetics of probe hybridization. Nevertheless, for a given probe, the signal intensities accurately reflected miRNA differential expression.

Example 3

Figure 15:
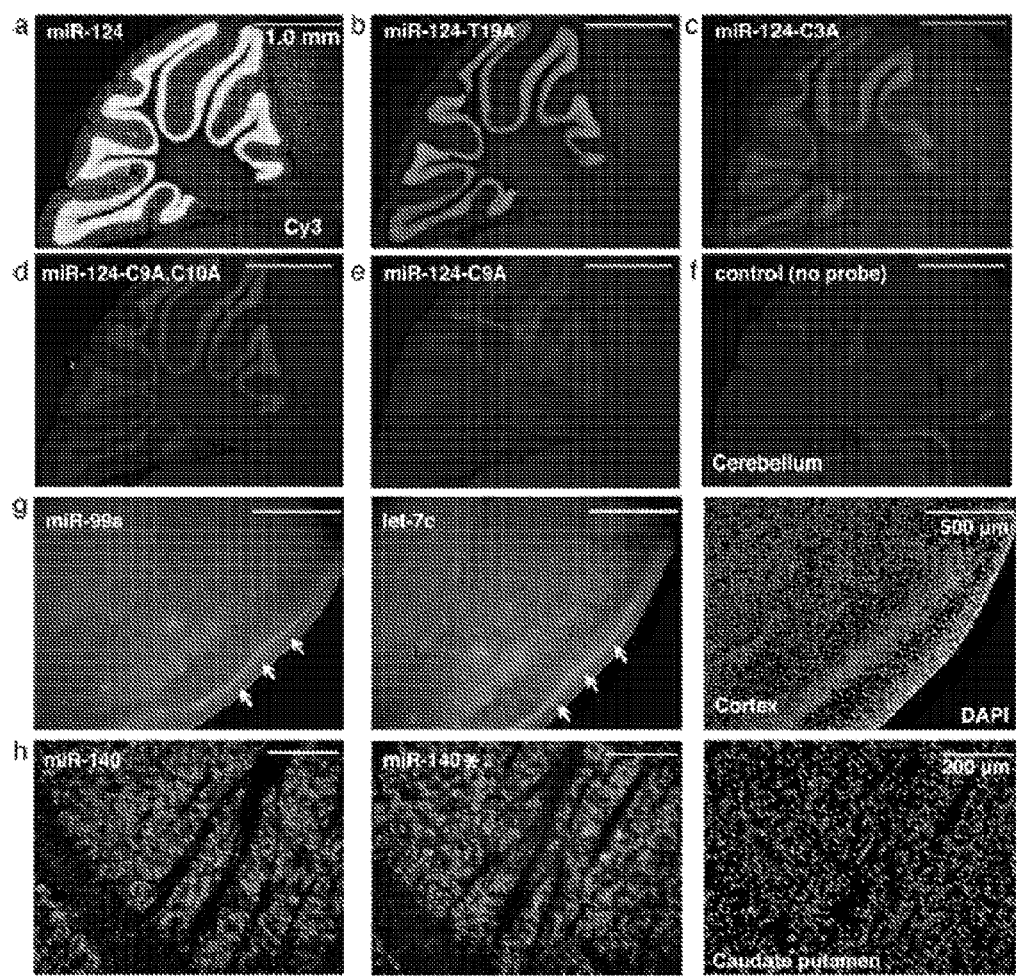
FIG. 15: Controls for miRNA probe specificity. (a) Images of neuron-specific miR-124 ISH (Cy3) of fully complementary probes show robust staining in the mouse cerebellum. miR-124 mismatch probes miR-124-T19A (b) and miR-124-C3A (c) signal is reduced but visible. MiR-124 mismatched near the middle or seed region, miR-124-C9A, C10A and miR-124-C9A respectively, show the least signal (d,e), similar to background (f). (g) Cistronically expressed miRNAs miR-99a (left, Cy3) and let-7c (center) exhibit similar band-like distributions in the cortex (Cy3; red), marked by arrows. Nuclei were counter-stained (right, DAPI; blue). (h) miR-140 (left, Cy3) and miR-140*(center, Cy3; red) co-localize in cortex and DAPI stain (left). Scale bars, 1.0 mm (a-f), 500 µm (g), 200 µm (h). For images (a-e), ISH was performed at 47.5° C., which was 20° C. below the $T_M$ of the perfect probe/miR-124 duplex determined at 1.5 µM strand concentrations. For image (g), a second gene copy of let-7c (clone count frequency 4.1%) is present in the cluster of mir-let-7c-2/mir-let-7b, which was approx. 2.5 fold more abundant than miR-let-7b (clone count frequency 1.7%).

To examine probe hybridization specificity, we selected miR-124 and introduced mismatches in the probe central regions. The ISH was performed at constant temperature 20° C. below the $T_M$ of the fully complementary miR-124 probe. The probes with the greatest difference in $T_M$ showed the least signal and central mismatches abolished detection (FIG. 15). Interestingly, signal strength observed for mismatched probes with minor reduction in $T_M$ dropped disproportionately, again indicative of altered kinetics of probe hybridization.

Example 4

Instead of a mismatch approach to control for probe specificity, conducting ISH using two probes directed against the mature miRNA and the opposing fragment in the miRNA duplex, known as the miRNA* sequence and/or clustered members may be useful to help rule out signals derived from cross-hybridization. We probed for cistronically expressed miRNAs that are distinct in sequence for colocalization, including members in the mir-99a/mir-125b-1/let-7c-1 cluster. The ISH for let-7c and miR-99a reveal mostly identical patterns that showed superimposable band-like patterns (FIG. 15g). Other let-7 family members also show similar expression, however, the signal observed in the band-like region of the cortex likely originated from let-7c due to colocalization of miR-99a. We also tested the miRNA* sequences as a specificity control for miRNA ISH signals. We examined miR-140 and its complementary miR-140* sequence, expressed at relative clone frequency of 5 to 1, respectively. The ISH with both probes revealed superimposible expression in the cortex (FIG. 15h).

Figure 3:
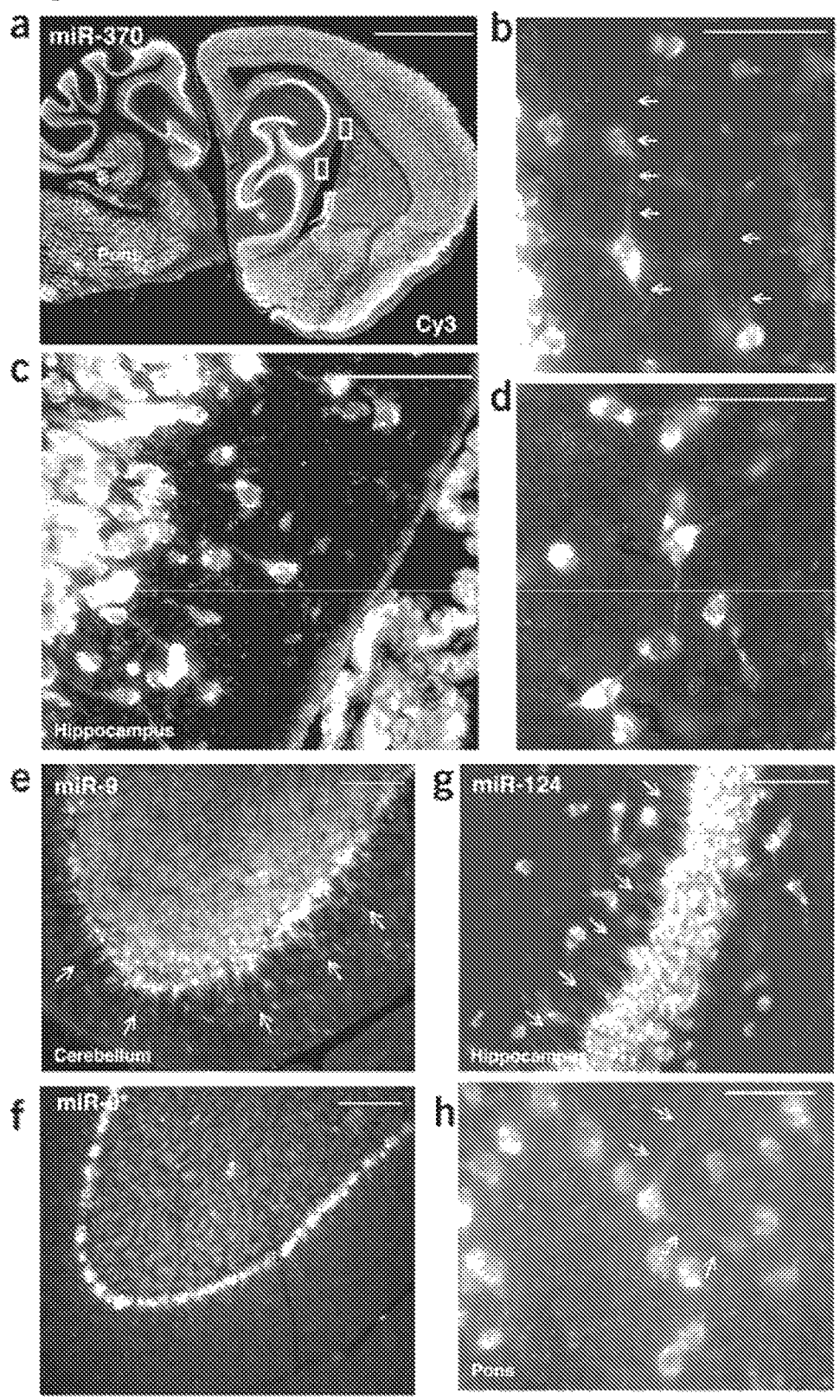
FIG. 3: Formaldehyde+EDC-fixed sections show miRNA localized in the dendrites of neurons. (a) Fluorescence micrographs of miR-370 expression detected with Cy3 (white) with intense staining in the hippocampus. (b-d) High magnification micrograph of the top boxed region in a, showing a single neutron in the CA1 region of the hippocampus for which miR-370 (Cy3, b) is localized both in the cell body and the dendrites (arrows, b). miR-370 (Cy3) shows staining up to 50 mm from the cell body (b), and 30 mM in other neurons (c,d) in the hippocampus, bottom boxed region in a represents hippocampus region shown in d. (e,f) Micrographs of the mature miR-9 (Cy3) expressed in Purkinje cells in the cerebellum (arrows point to dendrites; e) and miR-9*(Cy3), (f), which is absent in dendrites. (g,h) Pyramidal cells in the hippocampus (arrows) show staining of miR-124 (Cy3) in hippocampus dendrites (g) and in neurons located in the pons (h). Scale bars, 2 mm (a), 50 mm (b-d,g,h) and 100 mm (e,f).

Example 5 miRNAs are known to localize to subcellular compartments for local regulation of mRNA, possibly to the dendrites of neurons. We tested several miRNAs for expression in dendrites including miR-370 (FIG. 3a-d), miR-9 (FIG. 3e), and miR-124 (FIG. 3g,h), which extended up to 50 μm from the cell body. Interestingly, compared to miR-9, the 20-fold less expressed miR-9*, did not reveal localization in dendrites (FIG. 3f). Together, these data demonstrate this method detects miRNAs in subcellular compartments.

Example 6

Figure 16:
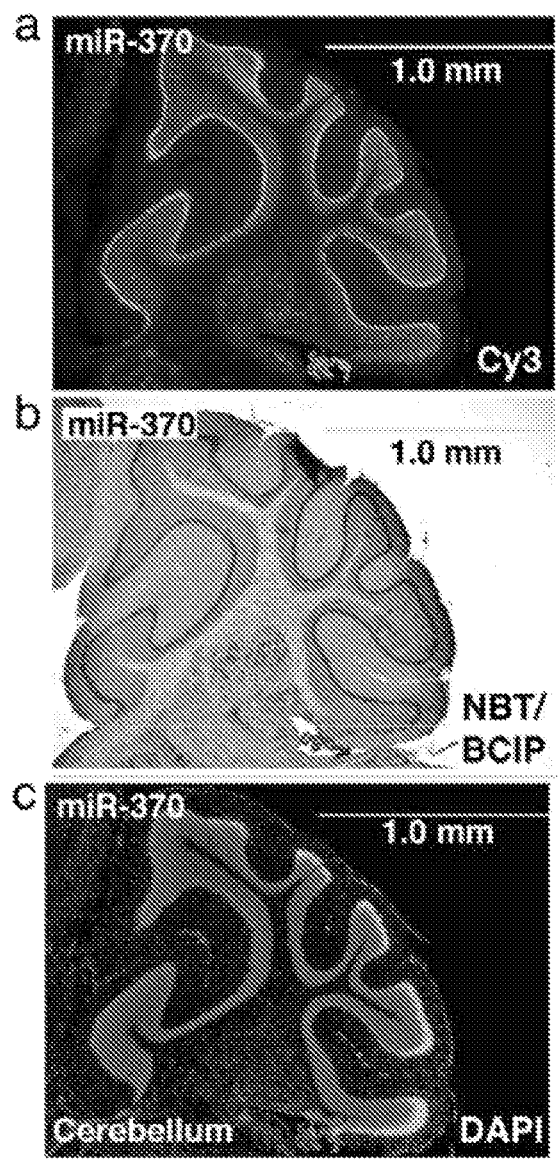
FIG. 16: Fluorescence and formazan deposition NBT/BCIP detection systems. (a) Fluorescent image of mouse brain cerebellum using Tyramide-Cy3 detection system. (b) Light microscopy image of serial sections of mouse brain cerebellum using NBT/BCIP detection system show similar cellular distribution as in fluorescent detection (a). (c) Images of DAPI nuclear stain. Scale bars, 1.0 mm (a-c).
Figure 17:
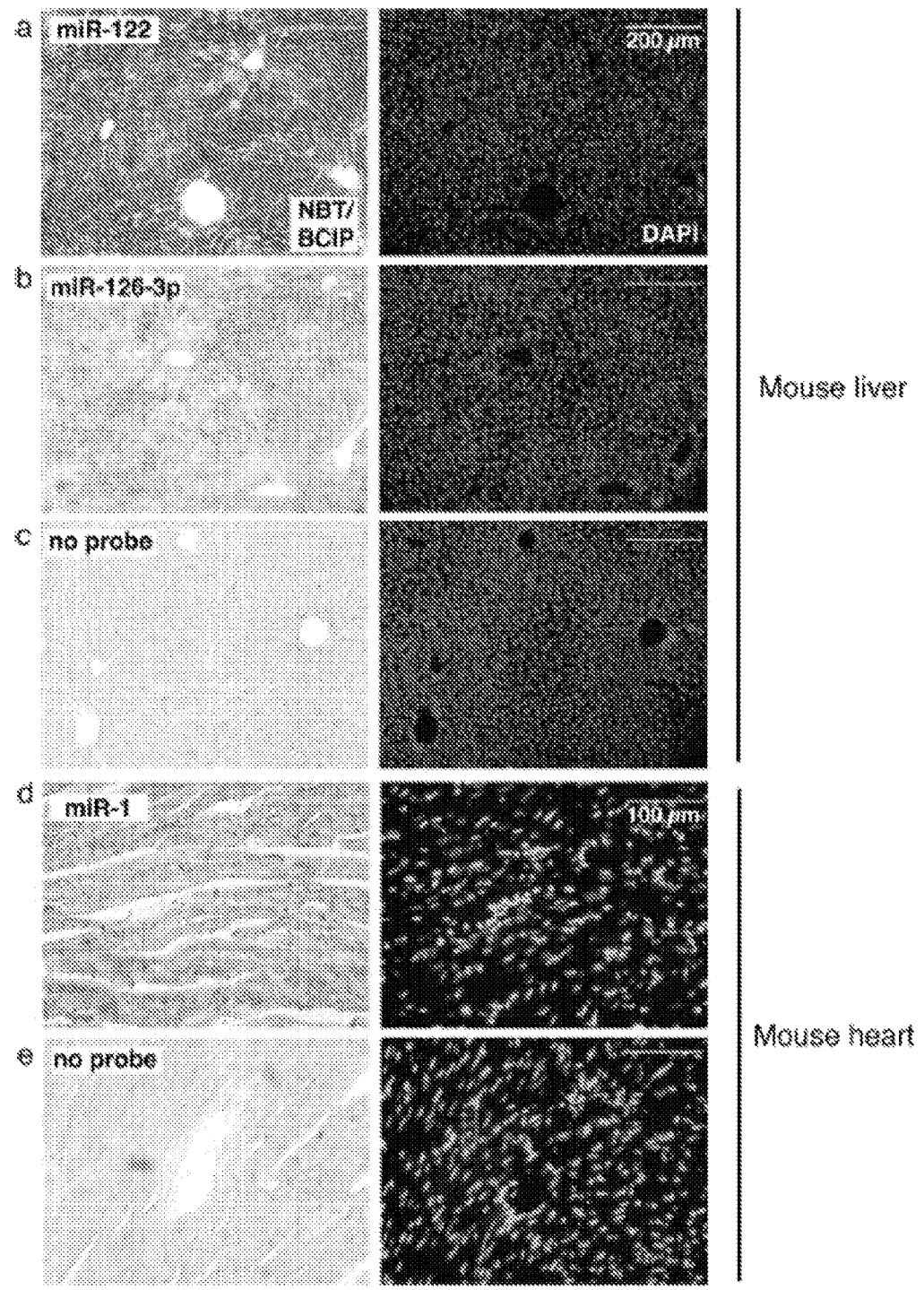
FIG. 17: Detection of miRNAs in mouse heart and liver sections using formazan deposition NBT/BCIP detection system. (a) Images of a highly abundant miR-122 ISH in the mouse liver sections, (b) the lower expressed miR-126, and a no probe control (c). (d) Images of the mouse heart sections show expression of highly abundant miR-1 (d), with a no probe, negative control (e). Cell nuclei were counterstained with DAPI (blue; right panel (a-e); Scale bars, 200 µm (a-e).

Finally, to broaden this technique for sections not amenable to fluorescent imaging, we compared the NBT/BCIP pigment detection system for miR-370 in the brain to fluorescent detection and observed similar staining (FIG. 16). We also tested the pigment detection for miR-122 and miR-126-3p in the mouse liver, miR-1 in the mouse heart, and observed cell-type-specific staining (FIG. 17). Furthermore, we combined the detection of proteins by immunohistochemistry with miRNA ISH (FIG. 14), although immunostaining that preceded EDC fixation reduced the signal strength for the miRNA ISH.

Example 7

Figure 4:
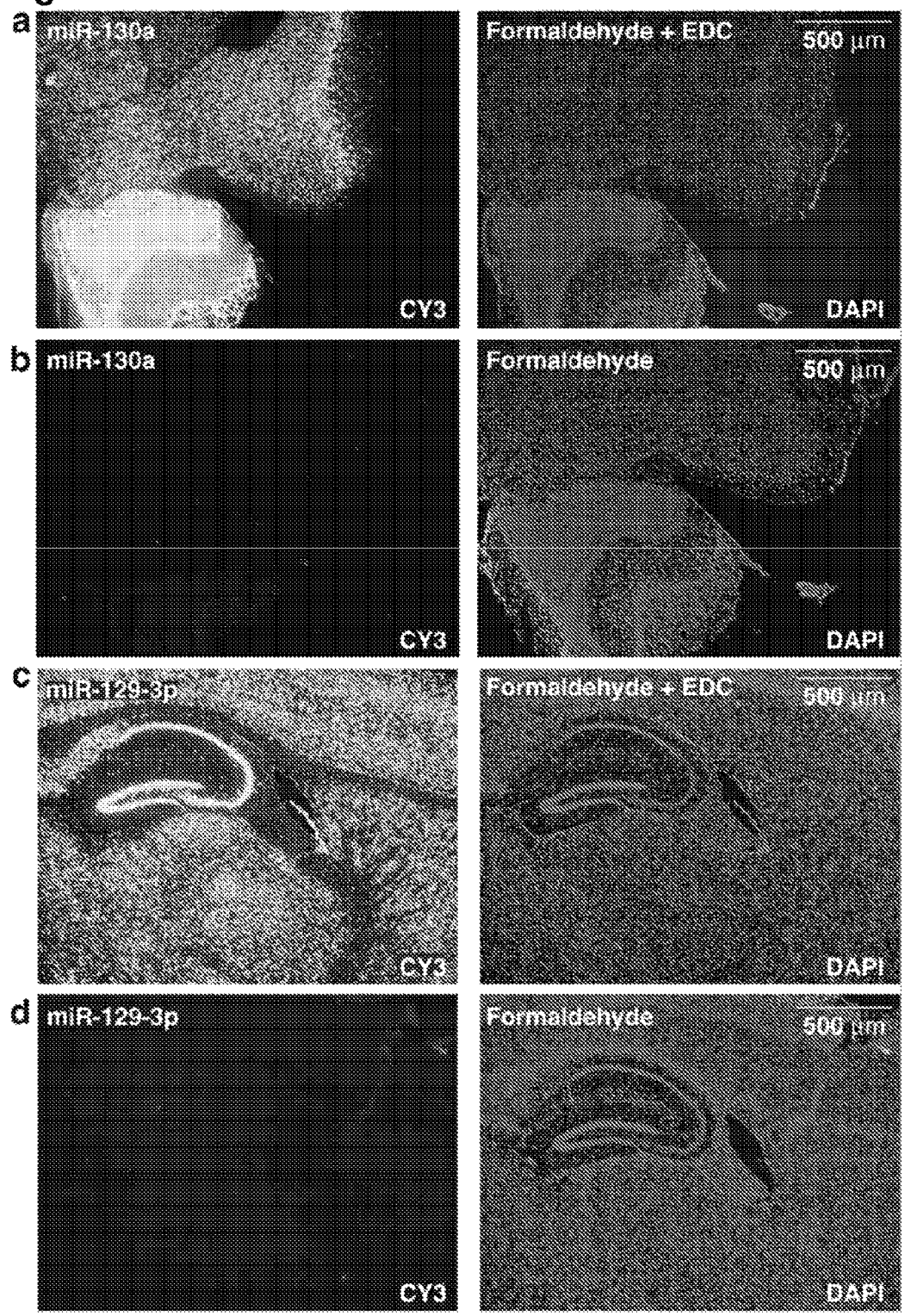
FIG. 4: Tissues fixed with formaldehyde-EDC substantially improves miRNA ISH signal for less abundant miR-NAs. (a) Low power fluorescent micrograph images ISH medium expressed miR-130a in regions of the olfactory bulb and cerebral cortex from mouse brain tissues fixed formaldehyde+EDC (a, Cy3; left) or formaldehyde alone (b, Cy3; left). (c) Low power fluorescent micrograph images of ISH for miR-129-3p (c, Cy3; left) in the hippocampus and cerebral cortex from mouse brain tissues fixed with formaldehyde and EDC (c, Cy3, left) or formaldehyde alone. Nuclei were stained (DAPI, a-d, right). Scale bars 500 µm in a-d.
Figure 5:
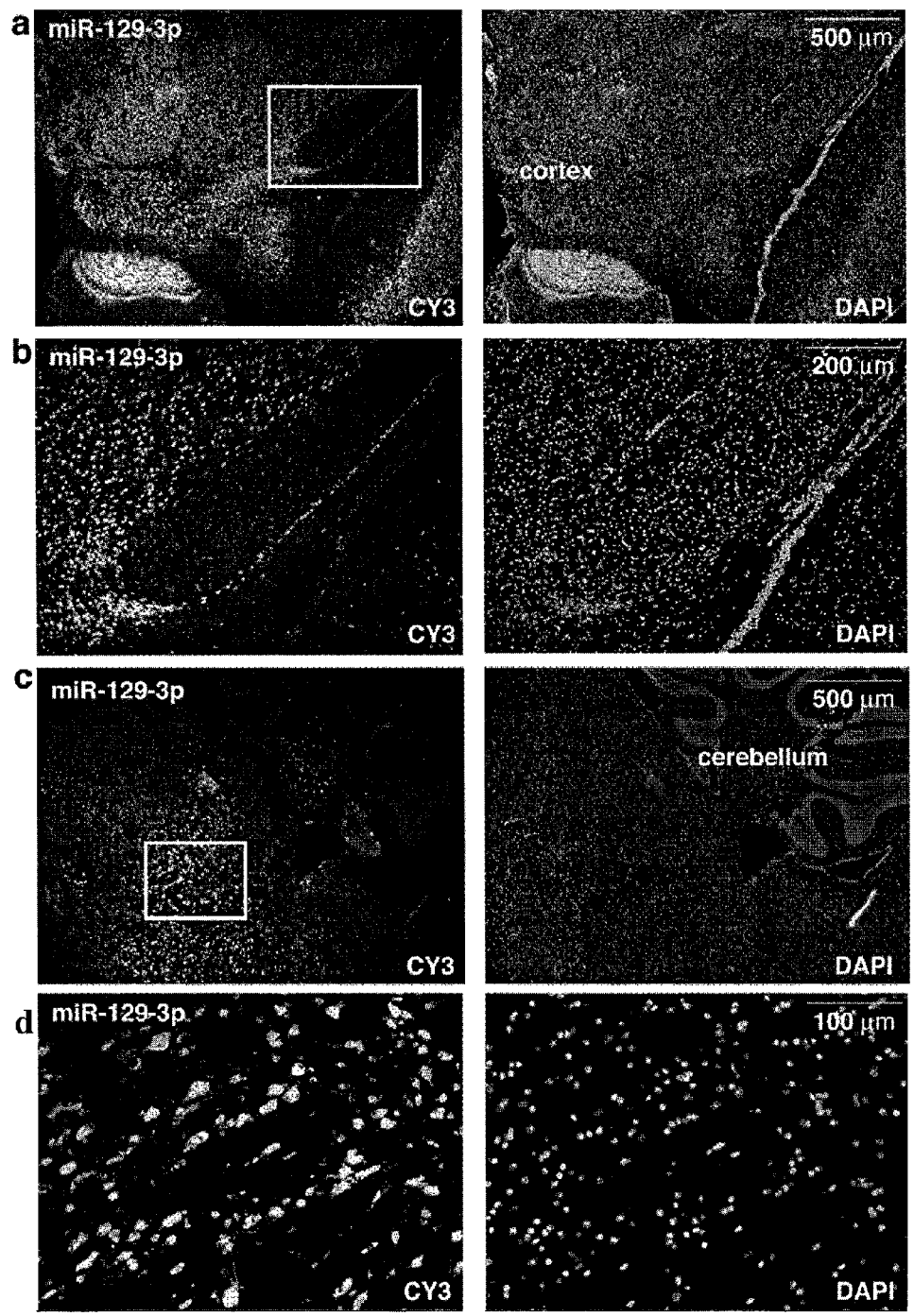
FIG. 5: Specific expression of miR-129-3p in the mouse brain and localization in dendrites. (a) Low power fluorescent micrograph images of the medium expressed miR-129-3p (Cy3; left) of the olfactory bulb and cerebral cortex and box in a represented in b, show higher magnification micrograph images with specific miR-129-3p expression in a single cell layer (b, Cy3, left). (c) Low power fluorescent micrograph images show miR-129-3p (Cy3; left) expression in the cerebellum, box in c shown with higher power magnification in panel d, show miR-129-3p (d, Cy3, left) expression in neuronal dendrites. Nuclei were stained (DAPI, right, a-d). Scale bars 500 µm in a, c; 200 µm in b; 100 µm in d.

To further improve the formaldehyde-EDC-based miRNA ISH procedure, we studied the less abundant miR-129-3p (clone count frequency 0.35%) and miR-130a (clone count frequency 0.12%), which show robust detection in formaldehyde-EDC fixed tissues (FIG. 4a, c; left), but the signal nearly blank in formaldehyde based ISH procedures (FIG. 4b, d; left). miR-129-3p showed expression in distinct brain areas (FIG. 5 a, b) and also expressed in the mouse hippocampus, cerebral cortex and cerebellum (FIG. 5, a-d).

Example 8

Figure 6:
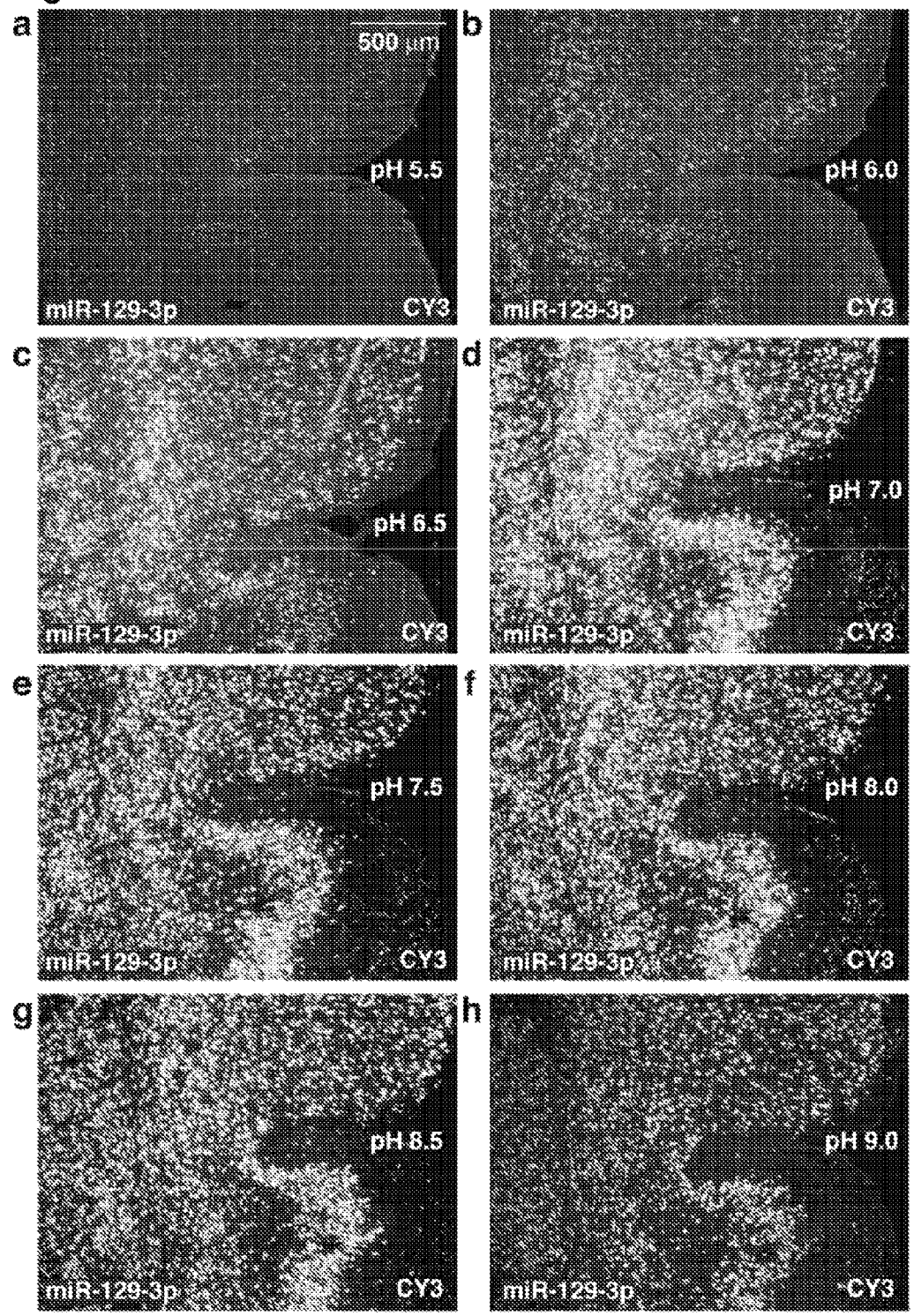
FIG. 6: miRNA ISH signal intensity is EDC fixation pH dependent. (a) Low power fluorescent micrograph images of tissues fixed with formaldehyde and then EDC solution at pH 5.5 (a) and 6.0 (b) show reduced signal for miR-129-3p (Cy3), compared to ISH signal for miR-129-3p in tissues fixed with EDC solution from pH 6.5 to 9.0 (d-h, Cy3). Scale bars 500 µm in a-h.
Figure 7:
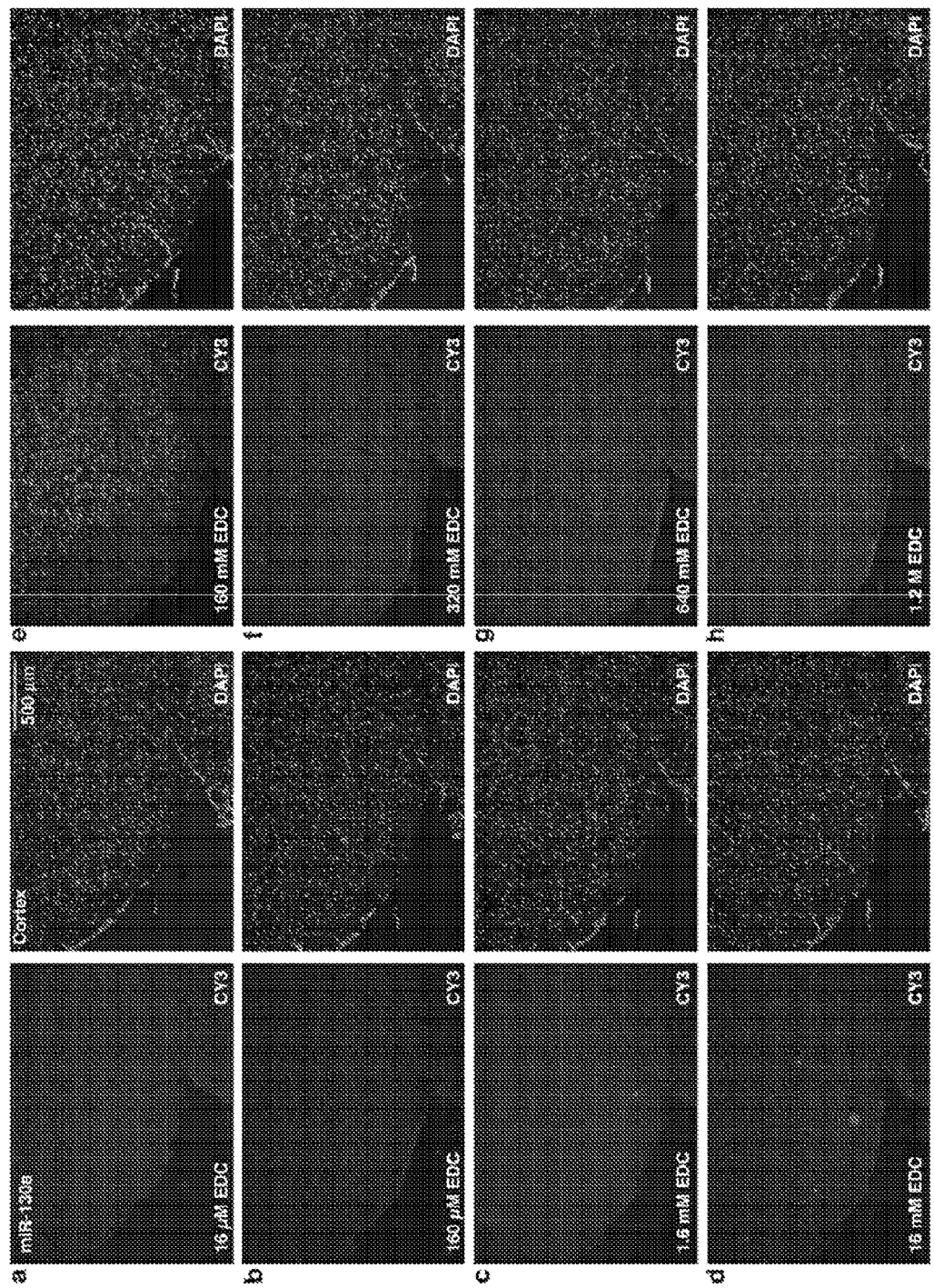
FIG. 7: EDC-based miRNA ISH is dependent on EDC concentration. (a-d) Low power fluorescent micrograph images of the medium expressed miR-130a (Cy3; left) fixed with formaldehyde-EDC at concentrations at or below 16 mM EDC (a-d, Cy3, left). (e) Low power fluorescent micrograph images show signal for miR-130a (e, Cy3; left) expression in the cortex with 160 mM EDC. (f-h) Low power fluorescent micrograph images of the medium expressed miR-130a (Cy3; left) fixed with formaldehyde-EDC at concentrations at or above 320 mM EDC (a-d, Cy3, left). Nuclei were stained (DAPI, blue; right, a-h). Scale bars 500 µm in a-h.

To determine if the formaldehyde-EDC miRNA ISH signal intensity is pH dependent, we treated formaldehyde fixed tissues with EDC solution in 1-methylimidazole buffer at pH 5.5 and 6.0, and observed notably weaker ISH signal for miR-129-3p (FIG. 6a, b), compared to tissues fixed with EDC solution at pH 6.5 and above (FIG. 6, c-h). The most intense miRNA ISH signal occurred using EDC solution at pH 7.0-8.5 (FIG. 6, c-g) and the signal becomes moderately less intense at pH 9.0 (FIG. 6h). To avoid loss of signal minor fluctuations in pH, we recommend working with EDC solution at pH 8.0 (FIG. 6f). We also examined the dose dependence of miRNA ISH signal intensity for various EDC concentrations diluted in 0.13 M imidazole buffer and pH adjusted to 8.0 (FIG. 7a-h), and the concentration of 0.16 M showed the brightest signal for miR-130a (FIG. 7e).

Example 9

We evaluated an alternative fixation reagent, with the goal of ligating the miRNA 5' phosphate to amino groups present in the formaldehyde fixed protein matrix, and examined the fixative cyanogen bromide (BrCN), which forms stable phosphoramidate cross-links by condensing phosphates to amino groups {Fedorova, 1996 #70}. We applied 0.5 M BrCN in 0.16 M N-morpholinoehanesulfonate (MES)-buffer (initial pH adjusted to 8.0) to formaldehyde fixed tissues for 1 h and processed the sections for miRNA ISH.

Figure 8:
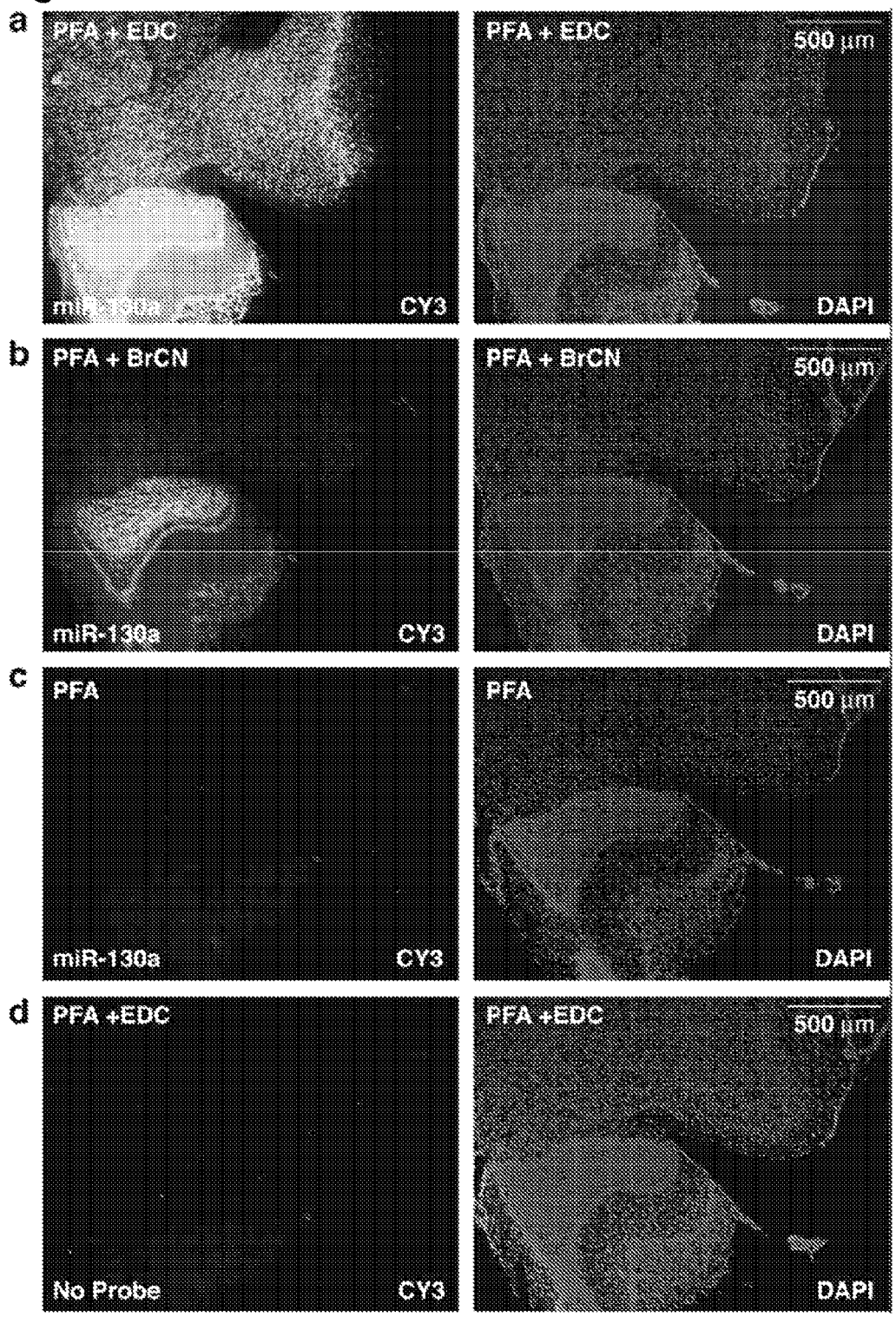
FIG. 8: Fixation with formaldehyde-cyanogen bromide (BrCN) enhances miRNA ISH detection in tissues. Fluorescent micrograph images of the mouse olfactory bulb and cerebral cortex show expression of miR-130a (Cy3) in tissue sections fixed with formaldehyde (PFA)-EDC fixation (a, Cy3; left), formaldehyde-BrCN fixation (b, Cy3; left), and formaldehyde fixation (c, Cy3; left). No probe control (d, Cy3; left). Nuclei were stained (DAPI, blue; right, a-d). Scale bars 500 µm in a-d.

We observed a notable improvement of the miRNA ISH signal for miR-129-3p in tissues fixed with formaldehyde-EDC and formaldehyde-BrCN (FIG. 8a, b), compared to signal from tissues fixed with formaldehyde alone (FIG. 8c).

Figure 9:
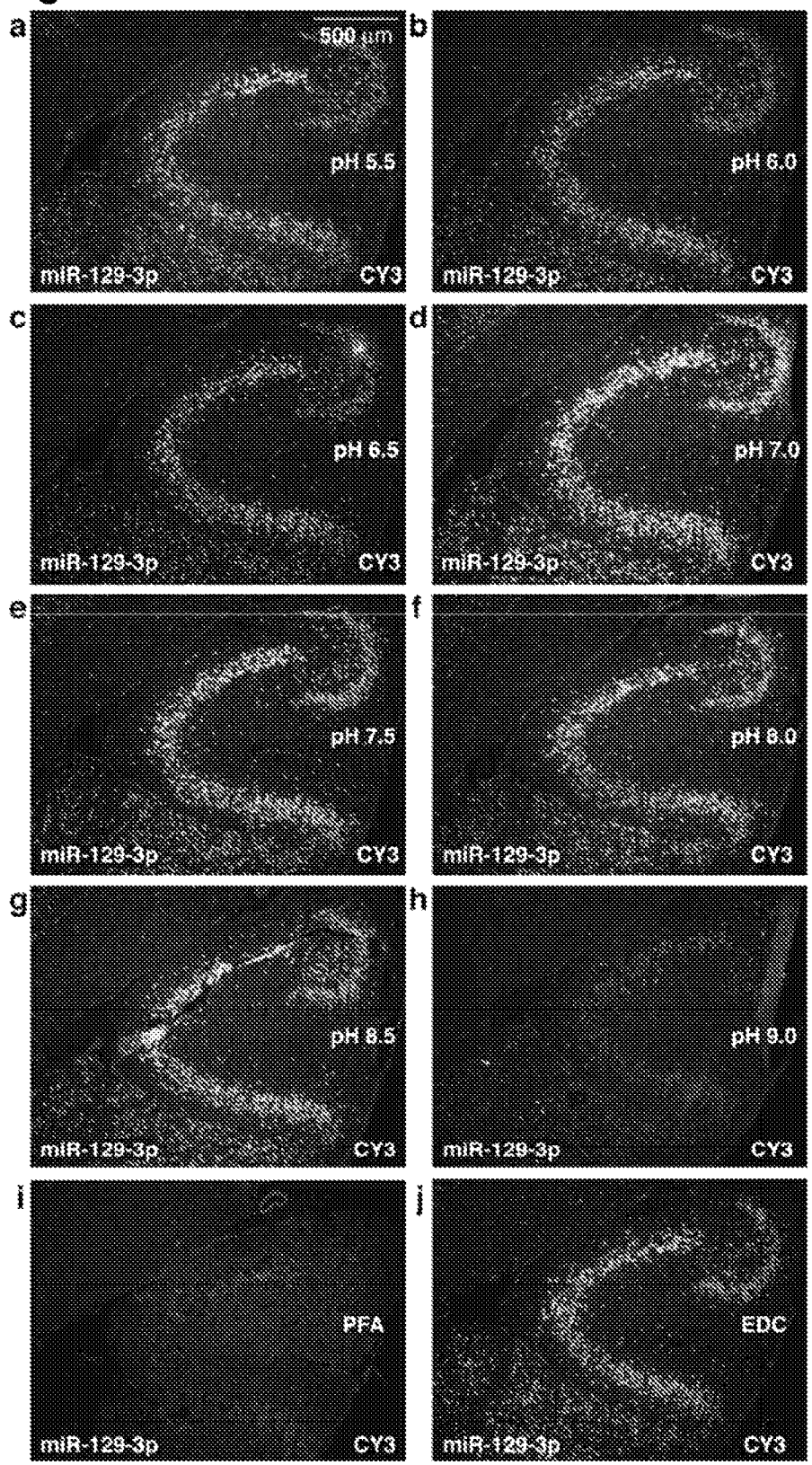
FIG. 9: formaldehyde-BrCN tissue fixation is pH dependent. (a) Low power fluorescent micrograph images of tissue sections of the mouse hippocampus from tissues fixed with formaldehyde-BrCN in MES buffer show expression of miR-129-3p (Cy3; a-h). Images of tissues fixed with formaldehyde and subsequent BrCN at pH solution at pH 5.5-8.5 show signal for miR-129-3p (FIG. 7, a-g, Cy3) compared to ISH signal for miR-129-3p in tissues fixed with formaldehyde-BrCN solution at pH 9.0 (h, Cy3), or tissues fixed with formaldehyde alone (i, Cy3). ISH signal at pH 7.0 showed the most intense staining (d), similar to formaldehyde-EDC (j, Cy3). Scale bars 500 µm in a-j.

We also examined the pH dependence for formaldehyde-BrCN solution. In tissues fixed with BrCN solutions diluted with MES-buffer at an initial pH 5.5-8.5, we observed a substantially improvement in miRNA ISH signal (FIG. 9 a-g), with the most intense signal at pH 7.0 (FIG. 9d), and almost no signal at pH 9.0 (FIG. 9h). When compared to tissues fixed with formaldehyde alone (FIG. 9i), applying formaldehyde BrCN at pH 7.0 substantially improved the signal (FIG. 9d), and formaldehyde-BrCN signal equaled the intensity of the formaldehyde-EDC fixed tissues (FIG. 9j).

Example 10

Figure 10:
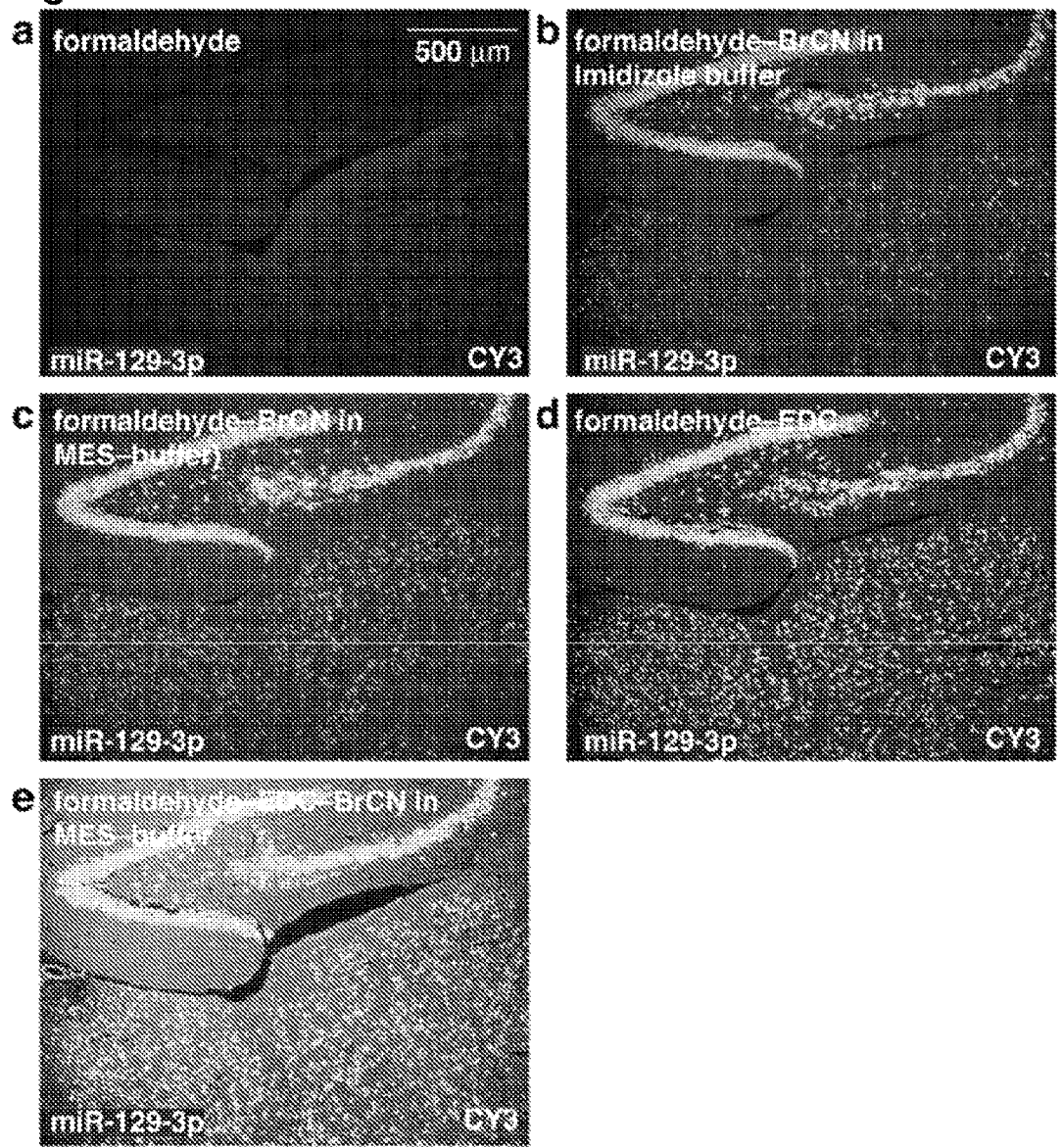
FIG. 10: Fixation of tissue samples with formaldehyde-EDC-BrCN improves microRNA detection in mammalian tissues. Fluorescent micrograph images of the mouse hippocampus show expression of miR-129-3p (Cy3) in tissue sections fixed with formaldehyde (a, Cy3), formaldehyde-BrCN solution in 1-methylimidazole buffer at pH 8.0 (b, Cy3), formaldehyde-BrCN solution in MES buffer at pH 7.0 (c, Cy3), formaldehyde-EDC solution diluted in 1-methylimidazole buffer at pH 8.0 (c, Cy3) and formaldehyde-EDC-BrCN (d, Cy3). Scale bars 500 µm in a-e.
Figure 11:
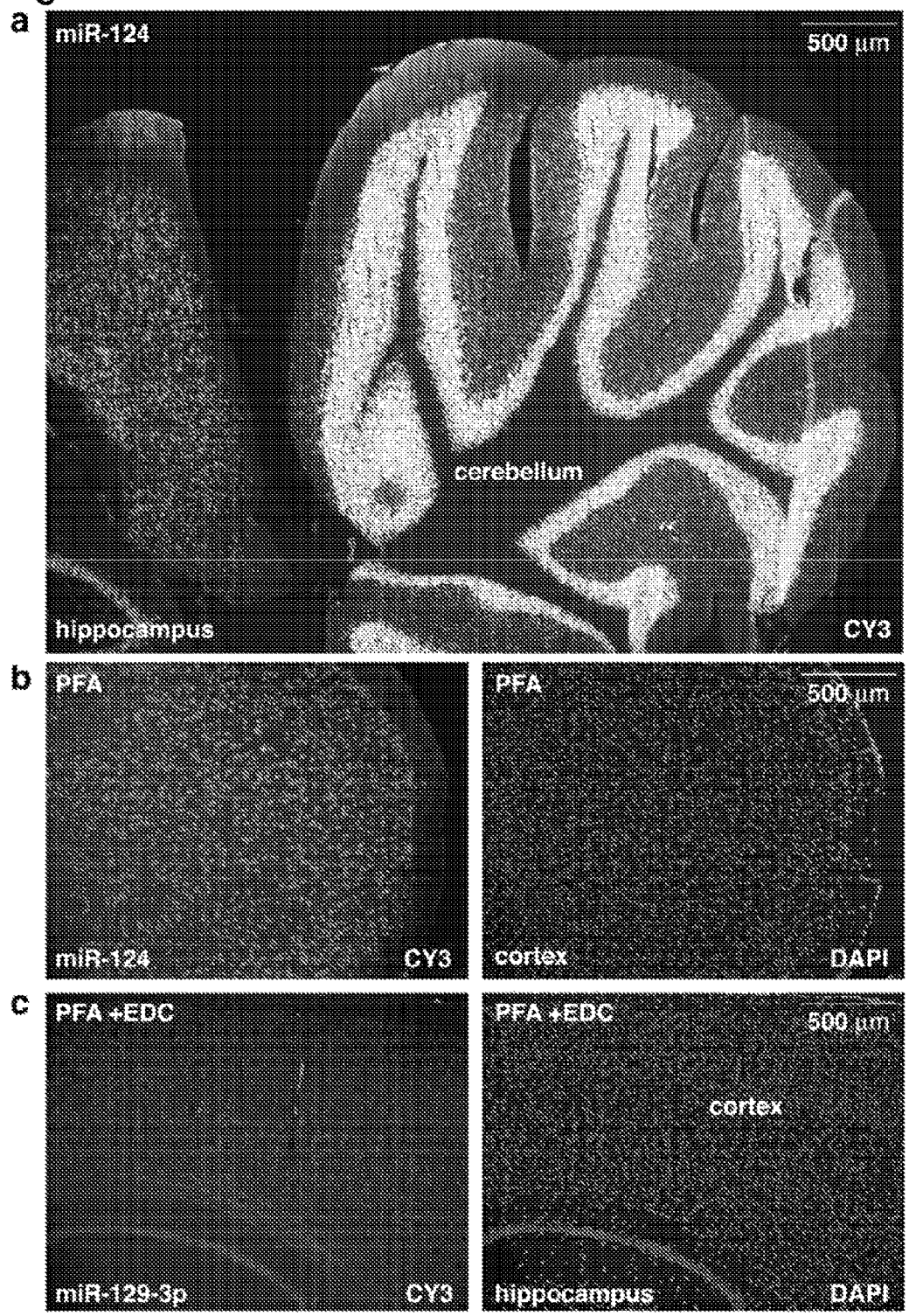
FIG. 11: Automation of formaldehyde-EDC miRNA ISH protocol. Fluorescent micrograph images of the mouse cerebellum show expression of miR-124 (Cy3) in tissue sections fixed with formaldehyde-EDC fixation (a, top, b, left Cy3), and miR-129-3p (c, left, Cy3). Nuclei were stained (DAPI, right, a-c). Scale bars 500 µm in b-c.
Figure 12:
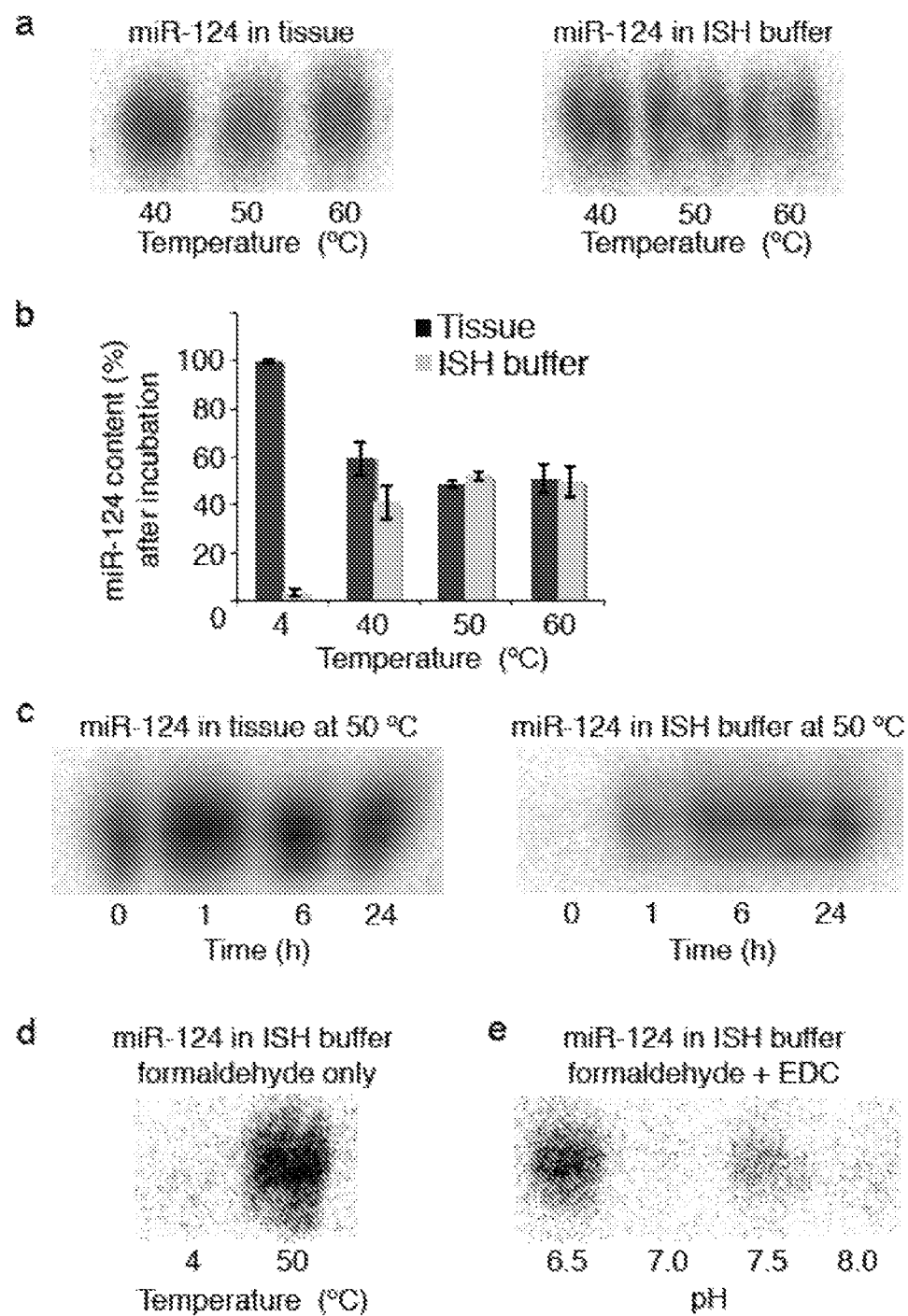
FIG. 12: miRNAs retained in formaldehyde+EDC fixed tissues. (a) Northern blotting analysis shows escape of miR-124 from formaldehyde-fixed tissues into ISH buffer after 24 h incubation at temperatures of 40° C. and higher. (b) Time course of hybridization at 50° C. shows miR-124 accumulates in ISH buffer after 1 h. (c) Quantification of Northern blots show approx. 50% of miR-124 were present in the hybridization buffer after overnight incubation, $P<0.05$, $n=3$. (d) At 4° C., miR-124 was not detectable in the hybridization buffer, which would suggest that RNA-protein crosslinks were intact at lower temperatures. (e) Samples fixed with formaldehyde+EDC show negligible amounts of miR-124 in ISH buffer at pH 7.0 and 8.0.

We examined combinations of formaldehyde, EDC, and BrCN in various sequence order (FIG. 10 a-e), and we observed the most intense miRNA ISH signal in tissues fixed with formaldehyde-EDC-BrCN (FIG. 10e, EDC solution diluted in 1-methylimidizole, pH adjusted to 8.0 and BrCN solution diluted in MES buffer, initial pH 7.0), when compared to other combinations (FIG. 10 a-e). Without being bound by theory, the improvements in miRNA ISH signal intensity may be due to differing mechanisms of action in condensing the miRNA 5' phosphate to the amino groups in the protein matrix. In the presence of an MES-buffer, BrCN forms the condensed products considerably faster (1-3 min), compared to the reaction rate of EDC in imidzole buffer (3-20 h), therefore the ligation mechanism of action likely differ {Fedorova, 1996 #70}. The reaction efficiency may depend on reacting groups or the adjacent nucleobases {Dolinnaya, 1994 #71}, therefore the combination of the fixatives may provide a wider coverage for miRNA which varying in sequence.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

What is claimed is:

1. A method for fixing a nucleic acid in a biological sample, said method comprising
    a) contacting the biological sample with an aldehyde-containing fixative; and
    b) subsequently contacting the sample with a water-soluble carbodiimide, wherein said carbodiimide is in solution with a buffer.

2. The method of claim 1, wherein the aldehyde-containing fixative is formaldehyde.

3. The method of claim 1, wherein the carbodiimide is selected from the group consisting of: 1-ethyl-3-(3-dimethylaminopropyl) carbodiimide (EDC); 1-Cyclohexyl-3-(2-morpholinyl-(4)-ethyl)carbodiimide metho-p-toluenesulfonate (CMC), N,N'-dicyclohexylcarbodiimide (DCC), and N,N'-diisopropylcarbodiimide (DIC).

4. The method of claim 3, wherein the carbodiimide is 1-ethyl-3-(3-dimethylaminopropyl) carbodiimide.

5. The method of claim 4, wherein the 1-ethyl-3-(3-dimethylaminopropyl) carbodiimide has a concentration of about 50 mM to about 250 mM.

6. The method of claim 4, wherein the 1-ethyl-3-(3-dimethylaminopropyl) carbodiimide contacts the sample at a temperature of about 20° C. to about 70° C.

7. The method of claim 4, wherein the carbodiimide has a pH of 8.0 in solution.

8. The method according to claim 1, wherein said nucleic acid is between 5-100 nucleotides.

9. A method for detecting a target nucleic acid in a biological sample, said method comprising a) contacting the biological sample with an aldehyde-containing fixative;
b) subsequently contacting the sample with a water-soluble carbodiimide to produce a crosslinked nucleic acid;
c) contacting the cross-linked nucleic acid with a probe, said probe being complementary to all or a part of a region of interest of the nucleic acid, thereby producing a hybridized nucleic acid; and
d) detecting the hybridized nucleic acid as the target nucleic acid.

10. The method of claim 9, wherein the carbodiimide is selected from the group consisting of: 1-ethyl-3-(3-dimethylaminopropyl) carbodiimide (EDC); 1-Cyclohexyl-3-(2-morpholinyl-(4)-ethyl)carbodiimide metho-p-toluenesulfonate (CMC), N,N'-dicyclohexylcarbodiimide (DCC), and N,N'-diisopropylcarbodiimide (DIC).

11. The method according to claim 10, wherein the carbodiimide is 1-ethyl-3-(3-dimethylaminopropyl) carbodiimide.

12. The method according to claim 11, wherein the 1-ethyl-3-(3-dimethylaminopropyl) carbodiimide has a concentration of about 50 mM to about 250 mM.

13. The method according to claim 11, wherein the 1-ethyl-3-(3-dimethylaminopropyl) carbodiimide has a temperature of about 20° C. to about 70° C.

14. The method according to claim 9, wherein the probe comprises a locked nucleic acid.

15. The method according to claim 9 wherein said nucleic acid is between 5-100 nucleotides.

\* \* \* \* \*